US010071162B2

(12) United States Patent
Aven et al.

(10) Patent No.: US 10,071,162 B2
(45) Date of Patent: Sep. 11, 2018

(54) PRESERVED ETHERIFIED CYCLODEXTRIN DERIVATIVES CONTAINING LIQUID AQUEOUS PHARMACEUTICAL COMPOSITION

(71) Applicants: Michael Aven, Mainz (DE); Tim Lukas, Heidersheim (DE)

(72) Inventors: Michael Aven, Mainz (DE); Tim Lukas, Heidersheim (DE)

(73) Assignee: BOEHRINGER INGELHEIM VETMEDICA GMBH (DE)

( * ) Notice: Subject to any disclaimer, the term of this patent is extended or adjusted under 35 U.S.C. 154(b) by 62 days.

(21) Appl. No.: 14/335,080

(22) Filed: Jul. 18, 2014

(65) Prior Publication Data
US 2015/0025082 A1 Jan. 22, 2015

(30) Foreign Application Priority Data
Jul. 19, 2013 (EP) ..................................... 13177268

(51) Int. Cl.
| A61K 31/50 | (2006.01) |
| A61K 31/501 | (2006.01) |
| A61K 47/40 | (2006.01) |
| A61K 9/00 | (2006.01) |
| A61K 9/08 | (2006.01) |
| A61K 47/69 | (2017.01) |

(52) U.S. Cl.
CPC ............ *A61K 47/40* (2013.01); *A61K 9/0095* (2013.01); *A61K 9/08* (2013.01); *A61K 31/501* (2013.01); *A61K 47/6951* (2017.08)

(58) Field of Classification Search
None
See application file for complete search history.

(56) References Cited

U.S. PATENT DOCUMENTS

| 3,574,859 A | 4/1971 | Kosti |
| 3,822,349 A | 7/1974 | Kosti |
| 3,832,460 A | 8/1974 | Kosti |
| 3,839,522 A | 10/1974 | Kosti |
| 3,950,333 A | 4/1976 | Durant et al. |
| 4,128,658 A | 12/1978 | Price et al. |
| 4,256,743 A | 3/1981 | Goldhaber |
| 4,283,400 A | 8/1981 | von Bittera et al. |
| 4,283,408 A | 8/1981 | Hirata et al. |
| 4,293,557 A | 10/1981 | Shibata et al. |
| 4,361,563 A | 11/1982 | Austel et al. |
| 4,375,547 A | 3/1983 | Pioch |
| 4,386,099 A | 5/1983 | Cereda et al. |
| 4,427,648 A | 1/1984 | Brickl et al. |
| 4,569,837 A | 2/1986 | Suzuki et al. |
| 4,585,790 A | 4/1986 | Padfield et al. |
| 4,596,705 A | 6/1986 | Schepky et al. |
| 4,654,342 A | 3/1987 | Slater |
| 4,704,284 A | 11/1987 | Beatty et al. |
| 4,732,915 A | 3/1988 | Ayer et al. |
| 4,851,226 A | 7/1989 | Julian et al. |
| 4,865,851 A | 9/1989 | James et al. |
| 4,868,182 A | 9/1989 | Dage |
| 4,906,628 A | 3/1990 | Coates |
| 4,933,182 A | 6/1990 | Higashi et al. |
| 4,954,501 A | 9/1990 | Herter et al. |
| 4,973,469 A | 11/1990 | Mulligan et al. |
| 5,024,998 A | 6/1991 | Bodor |
| 5,151,420 A | 9/1992 | Backstrom et al. |
| 5,188,836 A | 2/1993 | Muhammad et al. |

(Continued)

FOREIGN PATENT DOCUMENTS

| AU | 2012101682 A4 | 1/2013 |
| CA | 950833 A1 | 7/1974 |

(Continued)

OTHER PUBLICATIONS

Thiel et al., "Content uniformity of microdose tablets (dosage 1 µg-10 mg) produced by fluid bed granulation of interactive mixtures". Journal of Pharmacy and Pharmacology, vol. 38, 1986, pp. 335-343.

Petit et al., "VETMEDIN® 1.25 mg, VETMEDIN® 5 mg, Chewable tablets, Inodilator (pimobendan) tablet for dogs". Dictionary of Veterinary Drugs and Animal Health Products Marketed in France, 16th Edition, Les Editions du Point Vétérinaire, 2011, pp. 1658-1661.

"Vetmedin®—1,25 mg appetizing tablets for dogs Veterinary use". Summary of Product Characteristics, SCS Boehringer Ingelheim Comm. V, Mar. 25, 2009, pp. 1-4.

(Continued)

*Primary Examiner* — Jared D Barsky
(74) *Attorney, Agent, or Firm* — Judy Jarecki-Black

(57) ABSTRACT

The present invention is directed to a preserved liquid aqueous pharmaceutical composition comprising one or more etherified cyclodextrin derivatives; one or more water-soluble preservatives; preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; parabenes and salts thereof, preferably methylparabene, ethylparabene, propylparabene, butylparabene, butylparabene sodium; or combinations thereof; and at least one pharmaceutically active compound which is poorly water-soluble, very poorly water-soluble or water-insoluble. The liquid aqueous pharmaceutical composition provides an acceptable solubility of the pharmaceutically active compound, such as pimobendan, in aqueous solution whereby the water-soluble preservatives retain their effectiveness in the presence of the etherified cyclodextrin derivatives allowing the use in an oral administration form.

19 Claims, 3 Drawing Sheets

(56) References Cited

U.S. PATENT DOCUMENTS

| | | |
|---|---|---|
| 5,364,646 A | 11/1994 | Gruber et al. |
| 5,569,657 A | 10/1996 | Nore et al. |
| 5,571,533 A | 11/1996 | Santus et al. |
| 6,407,079 B1 | 6/2002 | Muller et al. |
| 6,476,078 B1 | 11/2002 | Jerussi et al. |
| 6,669,955 B2 | 12/2003 | Chungi et al. |
| 6,713,487 B2 | 3/2004 | Yu et al. |
| 7,262,165 B2 | 8/2007 | Lindenblatt et al. |
| 8,409,612 B1 | 4/2013 | Criere et al. |
| 8,846,679 B2 | 9/2014 | Folger et al. |
| 8,980,894 B2 | 3/2015 | Daemmgen et al. |
| 2003/0059471 A1 | 3/2003 | Compton et al. |
| 2003/0162835 A1 | 8/2003 | Staniforth et al. |
| 2003/0165565 A1 | 9/2003 | Mehta |
| 2003/0190343 A1 | 10/2003 | Thombre et al. |
| 2003/0212114 A1 | 11/2003 | Sato |
| 2004/0037869 A1 | 2/2004 | Cleverly et al. |
| 2004/0152664 A1 | 8/2004 | Chang et al. |
| 2004/0157887 A1 | 8/2004 | Whittle et al. |
| 2005/0095293 A1 | 5/2005 | Brauns et al. |
| 2005/0203097 A1 | 9/2005 | Folger et al. |
| 2005/0239692 A1 | 10/2005 | Lindenblatt et al. |
| 2007/0112010 A1 | 5/2007 | Kleeman et al. |
| 2008/0207629 A1* | 8/2008 | Folger ............... A61K 9/0019 514/252.02 |
| 2009/0082282 A1 | 3/2009 | Daemmgen et al. |
| 2010/0035889 A1 | 2/2010 | Daemmgen et al. |
| 2010/0166857 A1 | 7/2010 | Yan et al. |
| 2010/0183718 A1 | 7/2010 | Ovaert et al. |
| 2010/0273807 A1 | 10/2010 | Kleeman et al. |
| 2011/0028457 A1 | 2/2011 | Roewer et al. |
| 2011/0189283 A1 | 8/2011 | Derrieu et al. |
| 2011/0251208 A1 | 10/2011 | Daemmgen et al. |
| 2011/0318420 A1 | 12/2011 | Hu et al. |
| 2012/0148640 A1 | 6/2012 | Folger et al. |
| 2012/0308662 A1 | 12/2012 | Konishi et al. |
| 2013/0115301 A1 | 5/2013 | Bele et al. |
| 2013/0203690 A1 | 8/2013 | Daemmgen et al. |
| 2014/0155338 A1 | 6/2014 | Daemmgen et al. |
| 2015/0064249 A1 | 3/2015 | Folger et al. |
| 2015/0148335 A1* | 5/2015 | Bova ............... A61K 47/10 514/212.07 |
| 2015/0150820 A1 | 6/2015 | Laczay |
| 2016/0038420 A1 | 2/2016 | Brunel et al. |
| 2017/0290829 A1 | 10/2017 | Schummer et al. |

FOREIGN PATENT DOCUMENTS

| | | |
|---|---|---|
| CA | 1222697 A1 | 6/1987 |
| CA | 2034569 A1 | 7/1991 |
| CA | 1336498 C | 8/1995 |
| CN | 1662250 A | 8/2005 |
| CN | 1702243 A | 11/2005 |
| DE | 3728244 A1 | 3/1989 |
| DE | 4001623 A1 | 7/1991 |
| EP | 0241179 A1 | 10/1987 |
| EP | 0256566 A1 | 2/1988 |
| EP | 0268146 A1 | 5/1988 |
| EP | 0306846 A2 | 3/1989 |
| EP | 0330052 A2 | 8/1989 |
| EP | 0335545 A2 | 10/1989 |
| EP | 0349657 A1 | 1/1990 |
| EP | 439030 A2 | 7/1991 |
| EP | 1123703 A1 | 8/2001 |
| EP | 1247456 A2 | 10/2002 |
| EP | 1260215 A1 | 11/2002 |
| EP | 1579862 A1 | 9/2005 |
| EP | 1903039 A1 | 3/2008 |
| EP | 1920785 A1 | 5/2008 |
| EP | 2338493 A1 | 6/2011 |
| EP | 3034071 A1 | 6/2016 |
| FR | 2350105 A1 | 12/1977 |
| GB | 1045031 A | 10/1966 |
| GB | 2228004 A | 8/1990 |
| JP | 61500788 A | 4/1986 |
| JP | H029825 A | 1/1990 |
| JP | H0489428 A | 3/1992 |
| JP | H0570612 A | 3/1993 |
| JP | H11228302 A | 8/1999 |
| JP | 2005281283 A | 10/2005 |
| JP | 2007191419 A | 8/2007 |
| JP | 2008504308 A | 2/2008 |
| JP | 2011157390 A | 8/2011 |
| JP | 2012533595 A | 12/2012 |
| JP | 2013006798 A | 1/2013 |
| JP | 2013503113 A | 1/2013 |
| WO | 1985002767 A1 | 7/1985 |
| WO | 1989004178 A1 | 5/1989 |
| WO | 1995031963 A1 | 11/1995 |
| WO | 0012137 A1 | 3/2000 |
| WO | 2000069414 A2 | 11/2000 |
| WO | 2001035925 A1 | 5/2001 |
| WO | 2001064190 A1 | 9/2001 |
| WO | 2001097861 A2 | 12/2001 |
| WO | 0245693 A1 | 6/2002 |
| WO | 2002049646 A1 | 6/2002 |
| WO | 2003012030 A2 | 2/2003 |
| WO | 03072141 A1 | 9/2003 |
| WO | 2003074032 A1 | 9/2003 |
| WO | 2003075895 A1 | 9/2003 |
| WO | 2003097067 A1 | 11/2003 |
| WO | 2003099194 A2 | 12/2003 |
| WO | 2004000317 A1 | 12/2003 |
| WO | 2004000344 A1 | 12/2003 |
| WO | 2004016252 A1 | 2/2004 |
| WO | 2004033444 A1 | 4/2004 |
| WO | 2004050657 A2 | 6/2004 |
| WO | 2004058726 A2 | 7/2004 |
| WO | 2004060353 A1 | 7/2004 |
| WO | 2004089418 A1 | 10/2004 |
| WO | 2005035505 A2 | 4/2005 |
| WO | 2005084647 A1 | 9/2005 |
| WO | 2005092343 A1 | 10/2005 |
| WO | 2005107756 A1 | 11/2005 |
| WO | 2005117911 A2 | 12/2005 |
| WO | 2006000229 A2 | 1/2006 |
| WO | 2006022562 A1 | 3/2006 |
| WO | 2006060122 A2 | 6/2006 |
| WO | 2006060127 A2 | 6/2006 |
| WO | 2007036671 A2 | 4/2007 |
| WO | 2007038796 A1 | 4/2007 |
| WO | 2007054514 A2 | 5/2007 |
| WO | 2007112274 A2 | 10/2007 |
| WO | 2007128749 A1 | 11/2007 |
| WO | 2008055871 A1 | 5/2008 |
| WO | 2009060226 A1 | 5/2009 |
| WO | 2010010257 A2 | 1/2010 |
| WO | 2010055119 A2 | 5/2010 |
| WO | WO 2010055119 A2 * | 5/2010 ............ A61K 9/2013 |
| WO | 2010060874 A1 | 6/2010 |
| WO | 2011009818 A1 | 1/2011 |
| WO | 2011042463 A2 | 4/2011 |
| WO | 2011076738 A1 | 6/2011 |
| WO | 2013024023 A1 | 2/2013 |
| WO | 2013135852 A1 | 9/2013 |
| WO | 2013164473 A1 | 11/2013 |
| WO | 2013170317 A1 | 11/2013 |
| WO | 2014136035 A1 | 9/2014 |
| WO | 2015082389 A1 | 6/2015 |
| WO | 2017174571 A1 | 10/2017 |

OTHER PUBLICATIONS

"Rimadyl F 50 mg". Summary of Product Characteristics, Zoetis France, May 15, 2013, pp. 1-4.
Hemati et al., "Fluidized bed coating and granulation: influence of process-related variables and physicochemical properties on the growth kinetics". Powder Technology, vol. 13, 2002, pp. 18-34.
Abstract in English for JPH0489428, 1992.
Ash et al., "Receptor Mediating Some Actions of Histamine". British Journal of Pharmacology and Chemotherapy, vol. 27, No. 2, Aug. 1996, pp. 427-439.

(56) References Cited

OTHER PUBLICATIONS

Black et al., "Definition and Antagonism of Histamine H2-receptors". Nature, vol. 236, Apr. 1972, pp. 385-390.
Dews et al., "The Antihistamine Substance 2786 R.P." British Journal of Pharmacology, vol. 1, 1946, pp. 278-286.
Loew, Earl R., "Gastric Secretion in Dogs Treated with Histamine Antagonist, Thymoxyethyldiethylamine". Experimental Biology and Medicine, vol. 48, No. 1, Oct. 1941, pp. 65-68.
Lantz et al., "Stability of nizatidine in extemporaneous oral liquid preparations". American Journal of Hospital Pharmacy, vol. 47, No. 12, Dec. 1990, pp. 2716-2719.
Nakamoto et al., "The role of ascorbic acid deficiency in human gingivitis—a new hypothesis". Journal of Theoretical Biology, vol. 108, No. 2, May 1984, pp. 163-171.
Pernsteiner et al., "Effect of Topical Application of Phenylephrine Hydrochloride on Hyperplastic Gingivitis". Journal of Periodontology, vol. 48, No. 8, Aug. 1977, pp. 473-477.
Trendelenburg, U. "The Action of Histamine and 5-Hydroxytryptamine on Isolated Mammalian Atria". The Journal of Pharmacology and Experimental Therapeutics, vol. 130, No. 4, Dec. 1960, pp. 450-460.
Rackley, Charles E., "Diseases of the Heart and Pericardium"., The Merck Manual, Chapter 25, 16th Edition, 1992, pp. 446-459.
Remme et al., "Hemodynamic Effects of Intravenous Pimobendan in Patients with Left Ventricular Dysfunction". Journal of Cardiovascular Pharmacology, vol. 15, Supp. 2, 1989, pp. S41-S44.
Remme et al., "Hemodynamic, Neurohumoral, and Myocardial Energetic Effects of Pimobendan, a Novel Calcium-Sensitizing Compound, in Patients with Mild to Moderate Heart Failure". Journal of Cardiovascular Pharmacology, vol. 24, No. 5, 1994, pp. 730-739.
Rinsyo to Kenkyu, "A case of diastolic hypertrophic cardiomyopathy in which sinus bradycardia and associated cardiac failure were improved as a result of cilostazol administration." The Japanese Journal of Clinical and Experimental Medicine, vol. 83, No. 5, May 2006, pp. 125-130.
Rodriguez, Damon B., "Treatment of Feline Hypertrophic Cardiomyopathy". Compendium, vol. 24, No. 6, Jun. 2002, pp. 470-476.
Roland et al., "The Use of Pimobendan in Feline Heart Failure Secondary to Spontaneous Heart Disease". The 18th Annual ECVIM Congress, Abstract, Belgium, Sep. 2008, 1 page.
Rudnic et al., "Oral Solid Dosage Forms". Remington: The Science and Practice of Pharmacy, 20th Edition, Lippincott Williams & Wilkins, Baltimore, Maryland, Chapter 45, 2000, pp. 858-870.
Saavedra et al., "Reverse Remodeling and Enhanced Adrenergic Reserve From Passive External Support in Experimental Dilated Heart Failure". Journal of the American College of Cariology, vol. 39, No. 12, 2002, pp. 2069-1076.
Sabbah et al., "Effects of long-term monotherapy with enalapril, metoprolol, and digoxin on the progression of left ventricular dysfuntion and dilation in dogs with reduced ejection fraction". Circulation, vol. 89, 1994, pp. 2852-2859.
Sabbah, Hani N., "The Cardiac Support Device and the Myosplint: Treating Heart Failure by Targeting Left Ventricular Size and Shape". The Annals of Thoracic Surgery, vol. 75, 2003, pp. S13-S19.
Shiga et al., "b-Blocker Therapy Combined with Low-Dose Pimobendan in Patients with Idiopathic Dilated Cardiomyopathy and Chronic Obstructive Pulmonary Disease: Report on Two Cases". Cardiovascular Drugs and Therapy, vol. 16, 2002, pp. 259-263.
Sisson et al., "Myocardial Diseases of Dogs". Textbook of Canine and Feline Cardiology: Principles and Clinical Practice, Second Edition, Chapter 27, Saunders, 1999, pp. 581-619.
Sisson, David, "Lecture Notes: Cardiology", The District of Columbia Academy of Veterinary Medicine, May 2001, pp. 1-18.
Summerfield et al., "Efficacy of Pimobendan in the Prevention of Congestive Heart Failure or Sudden Death in Doberman Pinschers with Preclinical Dilated Cardiomyopathy (The Protect Study)". Journal of Veterinary Internal Medicine, vol. 26, 2012, pp. 1337-1349.
Takeda et al., "Normalization of Left Ventricular Parameters Following Combined Pimobendan and Carvedilol Treatment in a Case of Unclassified Cardiomyopathy with Longstanding Refractory Status". Internal Medicine, vol. 41, No. 12, Dec. 2002, pp. 1147-1152.
The American Heritage Dictionary, homogeneous, Last Accessed Feb. 10, 2011, 1 page, http://www.xreferplus.com/entry/hmdictenglang/homogeneous.
Tomanek et al., "Growth of the Coronary Vasculature in Hypertrophy: Mechanisms and Model Dependence". Cellular and Molecular Biology Research, vol. 40, No. 2, 1994, pp. 129-136.
Van Meel et al., "Pimobendan Increases Survival of Cardiomyopathic Hamsters". Journal of Cardiovascular Pharmacology, vol. 13, 1989, pp. 508-509.
Villar et al., "Ibuprofen, Aspirin and Acetaminophen Toxicosis and Treatment in Dogs and Cats". Veterinary and Human Toxicology, vol. 40, No. 3, Jun. 1998, pp. 156-162.
Wikipedia, the Free Encyclopedia, "Milrinone". [Accessed at: http://en.wikipedia.org/wiki/Milrinone on Mar. 10, 2014].
Wikipedia, the Free Encyclopedia, "Pimobendan". [Accessed at: http://en.wikipedia.org/wiki/Pimobenan on Mar. 10, 2014].
Woolley et al., "Effects of Treatment Type on Vertebral Heart Size in Dogs With Myxomatous Mitral Valve Disease". The Journal of Applied Research in Veterinary Medicine, vol. 5, No. 1, 2007, pp. 43-48.
Brewster et al., "Cyclodextrins as pharmaceutical solubilizers". Advanced Drug Delivery Reviews, vol. 59, No. 7, 2007, pp. 645-666.
Vidal et al., "Making sense of antisense". European Journal of Cancer, vol. 41, 2005, pp. 2812-2818.
Pirollo et al., "Targeted Delivery of Small Interfering RNA: Approaching Effective Cancer Therapies". Cancer Research, vol. 68, No. 5, Mar. 2008, pp. 1247-1250.
Phillips et al., "The challenge of gene therapy and DNA delivery". Journal of Pharmacy and Pharmacology, vol. 53, 2001, pp. 1169-1174.
"905 Uniformity of Dosage Units". 2011 The United States Pharmacopeial Convention, Stage 6 Harmonization, Dec. 1, 2011, pp. 1-3.
"Cardiovascular system". MIMS, IVS Annual, Chapter 5, 2003, p. 104.
"Citric Acid". The Merck Index, An Encyclopedia of Chemicals, Drugs, and Biologicals, 13th Edition, Merck Research Laboratories Division of Merck & Co., Inc., Whitehouse Station, NJ, Index 2350, 2001, pp. 405-406.
"Guidance for Industry, Container Closure Systems for Packaging Human Drugs and Biologics: Chemistry, Manufacturing, and Controils Documentation". U.S. Department of Health and Human Services Food and Drug Administration, May 1999, pp. 1-56.
"Pharmaceutical Necessities". Remington's Pharmaceutical Sciences, 18th Edition, Mack Publishing Company, Easton, Pennsylvania, Chapter 66, 1990, pp. 1288-1300.
"Pimobendan". The Merck Index, An Encyclopedia of Chemicals, Drugs, and Biologicals, 13th Edition, Merck Research Laboratories Division of Merck & Co., Inc., Whitehouse Station, NJ, Index 7515, 2001, p. 1332.
Abstract in English for CN1702243A, 2005.
Abstract in English for DE3728244,1989.
Abstract in English for EP0306846, 1989.
Abstract in English for EP0330052, 1989.
Abstract in English for JP2005281283, 2005.
Abstract in English of JPH0570612, 1993.
Abstract in English of JPH11228302, 1999.
Ahmed et al., "Pharmaceutical challenges in veterinary product development". Advanced Drug Delivery Reviews, vol. 54, 2002, pp. 871-882.
Asanoi et al., "Disparate Inotropic and Lusitropic Responses to Pimobendan in Conscious Dogs with Tachycardia-Induced Heart Failure". Journal of Cardiovascular Pharmacology, vol. 23, No. 2, 1994, pp. 268-274.

(56) References Cited

OTHER PUBLICATIONS

Atkins et al., "Guidelines for the Diagnosis and Treatment of Canine Chronic Valvular Heart Disease". Journal of Veterinary Internal Medicine, vol. 23, No. 6, 2009, pp. 1-9.
Banker et al., "Uniformity of Dosage Units". Modern Pharmaceutics, Fourth Edition, Revised and Expanded, Marcel Dekker, Inc., New York, NY, 2006, p. 498.
Bassani et al., "Enhanced Water-Solubility of Albendazole by Hydroxy-Propyl-β-Cyclodextrin Complexation". Journal of Inclusion Phenomena and Molecular Recognition in Chemistry, vol. 25, No. 1-3, Mar. 1996, pp. 149-152.
Bastien et al., "Chronic AT receptor blockade and angiotensin-converting enzyme (ACE) inhibition in (CHF 146) cardiomyopathic hamsters: effects on cardiac hypertrophy and survival". Cardiovascular Research, vol. 43, 1999, pp. 77-85.
Baur et al., "Cardiac remodelling and myocardial contractility in patients with congestive heart failure treated with furosemide and enalapril". Basic Research in Cardiology, vol. 86, Supp. 1, 1991, pp. 157-163.
Beers, et al., Merck Manual of Diagnosis and Therapy, 17th Edition, Chapter 203, Section 16, Merck Research Laboratories, Whitehouse Station, NJ, USA, 1999, pp. 1688-1692.
Berny et al., "Review: Animal Poisoning in Europe. Part 2: Companion Animals". The Veterinary Journal, vol. 193, 2010, pp. 255-259.
Boehringer Ingelheim Vetmedica GmbH, 1st International Canine Valvular Disease Symposium, Paris, Oct. 30-31, 2004, pp. 1-45.
Boehringer Ingelheim Vetmedica, Inc. "Freedom of Information Summary: Original New Animal Drug Application". NADA 141-273, Vetmedin, Pimobendan Chewable Tablets, Apr. 30, 2007, pp. 1-46.
Borgarelli et al., "Canine Idiopathic Dilated Cardiomyopathy. Part II: Pathophysiology and therapy". The Veterinary Journal, vol. 162, 2001, pp. 182-195.
Bozzone, Scott, "Solid Oral Dosage Forms Powder Blending" and "Solid Oral Dosage Forms, Blend Uniformity: Principles and Examples". Pfizer, IKEV Meeting, May 31, 2001, pp. 1-66.
Buchanan et al. "Vertebral scale system to measure canine heart size in radiographs". Journal of the American Veterinary Medical Association, vol. 206, No. 2, Jan. 1995, pp. 194-199.
Burlage et al., "Other Pharmaceutical Adjuncts"., Physical and Technical Pharmacy, The Blakiston Division: The McGraw-Hill Book Company, Inc., New York, 1963, pp. 653-662.
Calvert et al., "Congestive cardiomyopathy in Doberman Pinscher dogs". Journal of the American Veterinary Medical Association, vol. 181, 1982, pp. 598-602.
Calvert et al., "Signalment, Survival, and Prognostic Factors in Doberman Pinschers With End-Stage Cardiomyopathy". Journal of Veterinary Internal Medicine, vol. 11, No. 6, 1997, pp. 323-326.
Cambridge Dictionary, homogeneous, Last Accessed Feb. 10, 2011, 1 page, http://dictionary.cambridge.org/dictionary/british/homogeneous.
Chambers 21st Century Dictionary, homogeneous, Last Accessed Feb. 10, 2011, 1 page, http://www.xreferplus.com/entry/chambdict/homogeneous.
Chetboul, et al., "Comparitive Adverse Cardiac Effects of Pimobendan and Benazepril Monotherapy in Dogs with Mild Degenerative Mitral Valve Disease: A Prospective, Controlled, Blinded, and Randomized Study". Journal of Veterinary Internal Medicine, vol. 21, 2007, pp. 742-753.
Choy et al., "Scaling of myocardial mass to flow and morphometry of coronary arteries". Journal of Applied Physiology, vol. 104, 2008, pp. 1281-1286.
Cohn et al., "Cardiac Remodeling-Concepts and Clinical Implications: A Consensus Paper From an International Forum on Cardiac Remodeling". Journal of the American College of Cardiology, vol. 35, No. 3, 2000, pp. 569-582.
Collins English Dictionary, homogeneous, Last Accessed Feb. 20, 2011, 1 page, http://xreferplus.com/entry/hcengdict/homogeneous.
Conlon, P.D., "Nonsteroidal Drugs Used in the Treatment of Inflammation". Veterinary Clinics of North America: Small Animal Practice, vol. 18, No. 6, Nov. 1988, pp. 1115-1131.
Cowley et al, "Treatment of severe heart failure: quantity or quality of life? a trial of enoximone"., British Heart Journal, vol. 72, 1994, pp. 226-230.
Côté et al., "Congestive Heart Failure". Feline Cardiology, Ch. 19, Wiley-Blackwell, ISBN 978-0-8138-1242-7, 2011, p. 259.
Deneke et al., "Medikamentöse Therapie der Herzinsuffizienz". Herzschr Elektrophys, vol. 15, Suppl. 1, 2004, pp. 1/74-1/80.
Dictionary of Veterinary Drugs and Animal Health Products Marketed in France, 12th Edition, 2003, 3 pages.
El-Hagrasy et al., "A Process Analytical Technology Approach to Near-Infrared Process Control of Pharmaceutical Power Blending: Part II: Qualitative Near-Infrared Models for Prediction of Blend Homogeneity". Journal of Pharmaceutical Sciences, vol. 95, No. 2, Feb. 2006, pp. 407-421.
El-Hagrasy et al., "Near-Infrared Spectroscopy and Imaging for the Monitoring of Powder Blend Homogeneity". Journal of Pharmaceutical Sciences, vol. 90, No. 9, Sep. 2001, pp. 1298-1307.
Elliott, P., "Diagnosis and management of dilated cardiomyopathy". Heart, vol. 83, 2000, pp. 106-112.
Endoh, Masao, "New Aspects of the Treatment of Myocardial Failure from a Pharmacological Standpoint". Journal of Clinical and Experimental Medicine, vol. 187, No. 10, 1998, pp. 827-831.
Erhardt, L., "An Emerging Role for Calcium Sensitisation in the Treatment of Heart Failure". Expert Opinion on Investigational Drugs, vol. 14, No. 6, 2005, pp. 659-670.
Ettinger et al., "Effects of enalapril maleate on survival of dogs with naturally acquired heart failure". Journal of the American Veterinary Medical Association, vol. 213, No. 11, 1998, pp. 1573-1577.
Fitton et al., "Pimobendan. A Review of its Pharmacology and Therapeutic Potential in Congestive Heart Failure". Drugs and Aging, vol. 4, No. 5, 1994, pp. 417-441.
Fox et al., "Prosepective Double-Blinded, Multicenter Evaluation of Chronic Therapies for Feline Diastolic Heart Failure: Interim Analysis". ACVIM Abstracts, Abstract 78, 2003, pp. 398-399.
Fox, Philip R., "Hypertrophic Cardiomyopathy. Clinical and Pathologic Correlates". Journal of Veterinary Cardiology, vol. 5, No. 2, Nov. 2003, pp. 39-45.
Ettinger et al., "Therapeutic Considerations in Medicine and Disease". Textbook of Veterinary Internal Medicine, Diseases of the Dog and Cat, Sixth Edition, vol. I, 2004, pp. 530-531.
Fuentes, et al., "A Double-Blind, Randomized, Placebo-Controlled Study of Pimobendan in Dogs with Dilated Cardiomyopathy," Journal of Veterinary Internal Medicine, vol. 16, 2002, pp. 255-261.
Fujino et al., "Differential Effects of d- and l-Pimobendan on Cardia Myofilament Calcium Sensitivity". The Journal of Pharmacology and Experimental Therapeutics, vol. 247, No. 2, 1988, pp. 519-523.
Goineau et al., "Cardiomyopathic Syrian Hamster as a Model of Congestive Heart Failure". Current Protocols in Pharmacology, Supp. 42, Unit 5.50, John Wiley & Sons, Inc., Sep. 2008, 12 pages.
Groban, Leanne, "Diastolic Dysfunction in the Older Heart". Journal of Cardiothoracic and Vascular Anesthesia, vol. 19, No. 2, Apr. 2005, pp. 228-236.
Gwathmey et al., "Abnormal Intracellular Calcium Handling in Myocardium From Patients With End-Stage Heart Failure". Circulation Research, vol. 61, No. 1, 1987, pp. 70-76.
Hasenfuss et al., "Influence of the calcium-sensitizer UDCG-115 on hemodynamics and myocardial energetics in patients with idiopathic dilated cardiomyopathy. Comparison with nitroprusside". Basic Research Cardiology, vol. 84, No. 1, 1989, pp. 225-233.
Hauf et al., "Acute and Long-Term Hemodynamic Effects of Pimobendan (UD-CG 115 BS) in Comparison with Captopril". Journal of Cardiovascular Pharmacology, vol. 15, Supp. 2, 1989, pp. S49-S56.
Häggstrom et al., "Effect of Pimobendan or Benazepril Hydrochloride on Survival Times in Dogs with Congestive Heart Failure Caused by Naturally Occurring Myxomatous Mitral Valve Disease: The Quest Study". Journal of Veterinary Internal Medicine, vol. 22, 2008, pp. 1124-1135.
Häggstrom et al., "Longitudinal Analysis of Quality of Life, Clinical, Radiographic, Echocardiographic, and Laboratory Variables in

(56) References Cited

OTHER PUBLICATIONS

Dogs with Myxomatous Mitral Valve Disease Rexceiving Pimobendan or Benazepril: The QUEST Study". Journal of Veterinary Internal Medicine, 2013, pp. 1-11.

Häggström et al., "Effects of long-term treatment with enalapril or hydralazine on the renin-angiotension-aldosterone system and fluid balance in dogs with naturally acquired mitral valve regurgitation". American Journal of Veterinary Research, vol. 57, No. 11, Nov. 1996, pp. 1645-1662.

Häggström et al., "New insights into degenerative mitral valve disease in dogs". Veterinary Clinics Small Animal Practice, vol. 34, 2004, pp. 1209-1226.

Iwasaki et al., "Pimobendan Inhibits the Production of Proinflammatory Cytokines and Gene Expression of Inducible Nitric Oxide Synthase in a Murine Model of Viral Myocarditis". Journal of the American College of Cardiology, vol. 33, No. 5, 1999, pp. 1400-1407.

Jain et al., "Effects of Milrinone on Left Ventricular Remodeling After Acute Myocardial Infarction". Circulation, vol. 84, No. 2, Aug. 1991, pp. 798-804.

Kashem et al., "CardioClasp: A New Passive Device to Reshape Cardiac Enlargement". ASAIO Journal, vol. 48, No. 3, 2002, pp. 253-259.

Kato et al., "Clinical Evaluation of Pimobendan (UD-CG115BS) for Chronic Heart Failure—A Multicentre Placebo-Controlled Double Blind Study". Journal of Clinical Therapeutics & Medicines, vol. 8, No. 6, 1992, pp. 1311-1351.

Kato, Kazuzo, "Clinical Efficacy and Safety of Pimobendan in Treatment of Heart Failure-Experience in Japan". Cardiology, vol. 88, Supp. 2, 1997, pp. 28-36.

Katz et al., "A multicenter, randomized, double-blind, placebo-controlled trial of pimobendan, a new cardiotonic and vasodilator agent, in patients with severe congestive heart failure". American Heart Journal, vol. 123, 1992, pp. 95-103.

Kittleson et al., "The Acute Hemodynamic Effects of Milrinone in Dogs With Severe Idiopathic Myocardial Failure". Journal of Veterinary Medicine, vol. 1, 1987, pp. 121-127.

Koob et al., "Acute Effects of Furosemide on Blood Electrolytes and Hemodynamics in Dogs". Angiology, 1978, pp. 463-472.

Kubo et al, "Beneficial Effects of Pimobendan on Exercise Tolerance and Quality of Life in Patients with Heart Failure. Results of a Multicenter Trial". Circulation, vol. 85, No. 3, Mar. 1992, pp. 942-949.

Kvart et al., "Efficacy of Enalapril for Prevention of Congestive Heart Failure in Dogs with Myxomatous Valve Disease and Asymptomatic Mitral Regurgitation". Journal of Veterinary Internal Medicine, vol. 16, 2002, pp. 80-88.

Lachman et al., "The Theory and Practice of Industrial Pharmacy"., 3rd Edition, Lea & Febiger, Philadelphia, 1986, pp. 58-60.

Lai et al., "Real Time and Noninvasive Monitoring of Dry Powder Blend Homogeneity". AIChE Journal, vol. 47, No. 11, Nov. 2001, pp. 2618-2622.

Lamb et al., "Assessment of the value of the vertebral heart scale in the radiographic diagnosis of cardia disease in dogs". Veterinary Record, vol. 146, 2000, pp. 687-690.

Lewis et al., "Near-Infrared Chemical Imaging for Product and Process Understanding". in Process Analytical Technology, Second Edition, John Wiley & Sons, Ltd., United Kingdom, 2010, pp. 272-276.

Lewis, Alan B., "Clinical Profile and Outcome of Restrictive Cardiomyopathy in Children". American Heart Journal, vol. 123, No. 6, 1992, pp. 1589-1593.

Lip et al., "ABC of heart failure: Aetiology". British Medical Journal, vol. 320, Jan. 2000, pp. 104-107.

Liu et al., "Cardiovascular Pathology: The Role of Cardiovascular Pathology in Practice". Textbook of Canine and Feline Cardiology: Principles and Clinical Practice, Second Edition, Chapter 36, Saunders, 1999, pp. 817-844.

Loftsson et al., "Pharmaceutical Applications of Cyclodextrins. 1. Drug Solubilization and Stabilization". Journal of Pharmaceutical Sciences, vol. 85, No. 10, Oct. 1996, pp. 1017-1025.

Lombard et al., "Clinical Efficacy of Pimobendan Versus Benazepril for the Treatment of Acquired Atrioventricular Valvular Disease in Dogs". Journal of the American Animal Hospital Association, vol. 42, No. 4, Jul./Aug. 2006, pp. 249-261.

Lombard, Christophe W., "Therapy of Congestive Heart Failure in Dogs with Pimobendan". Proceedings of the 18th Annual Veterinary Medical Forum, American College of Veterinary Internatl Medicine, Seattle, WA, 2000, pp. 107-1093.

Lord et al., "Radiology: Role of Radiology in Diagnosis and Management of Thoracic Disease". Textbook of Canine and Feline Cardiology: Principles and Clinical Practice, Second Edition, Chapter 7, Saunders, 1999, pp. 111-117.

Luis-Fuentes, Virginia, "The effect of pimobendan in English Cocker Spaniels and Doberman dogs with heart failure and idiopathic dilated cardiomyopathy (DCM)". Ingelheimer Dialog, Boehringer Inglehim Vetmedica GmbH, Jun. 2000, Frankfort/Mainz, pp. 8-11.

Lyon et al., "Near-Infrared Spectral Imaging for Quality Assurance of Pharmaceutical Products: Analysis of Tablets to Assess Powder Blend Homogeneity". AAPS PharmSciTech, vol. 3, No. 3, Art 17, Sep. 2002, pp. 1-15.

Malik et al., "Permethrin Spot-On Intoxication of Cats: Literature review and survey of veterinary practitioners in Australia". Journal of Feline Medicine and Surgery, vol. 12, 2010, pp. 5-14.

Mamoru et al., "Effects of Long-term, Very-low-dose Pimobendan for Patients with Diastolic Heart Failure". Journal of Cardial Failure, vol. 12, No. 8, Oct. 2006, p. S171.

Matsumori et al., "Pharmacology letters: Accelerated Communication: Pimobendan inhibits the activation of transcription factor NF-kB A mechanism which explains its inhibition of cytokine production and inducible nitric oxide synthase". Life Sciences, vol. 67, 2000, pp. 2513-2519.

McCrohon et al., "Differentiation of Heart Failure Related to Dilated Cardiomyopathy and Coronary Artery Disease Using Gadolinium-Enhanced Cardiovascular Magnetic Resonance". Circulation, vol. 108, Jul. 2003, pp. 54-59. Originally published online Jun. 23, 2003, http://circ.ahajournals.org, 7 pages.

Medline, homogeneous, Merriam-Webster, Last Accessed Feb. 10, 2011, 1 page, http://www.merriam-webster.com/medlineplus/homogeneous.

Menard et al., "Physico-Chemical Aspects of the Complexation of Some Drugs with Cyclodextrins". Drug Development and Industrial Pharmacy, vol. 16, No. 1, 1990, pp. 91-113.

Merriam-Webster, homogeneous, Last Accessed Feb. 10, 2011, 2 pages, http://www.merriam-webster.com/dictionary/homogeneous.

Monnet et al., "Idiopathic Dilated Cardiomyopathy in Dogs: Survival and Prognostic Indicators". 1995, Journal of Veterinary Internal Medicine, vol. 9, No. 1, pp. 12-17.

Ng, Tien M.H., "Levosimendan, a New Calcium-Sensitizing Inotrope for Heart Failure". Pharmacotherapy, vol. 24, No. 10, 2004, pp. 1366-1384.

O'Grady, et al., "Does Angiotensin Converting Enzyme Inhibitor Therapy Delay the Onset of Congestive Heart Failure or Sudden Death in Doberman Pinschers with Occult Dilated Cardiomyopathy?" Acvim Abstracts, 1997, p. 138.

Ohte et al., "The Cardia Effects of Pimobendan (But Not Amrinone) Are Preserved at Rest and During Exercise in Conscious Dogs with Pacing-Induced Heart Failure". The Journal of Pharmacology and Experimental Therapeutics, vol. 282, No. 1, 1997, pp. 23-31.

Okazaki et al., "A genetic linkage map of the Syrian hamster and localization of cariomyopathy locus on chromosome 9qa2.1-b1 using RLGS spot-mapping". Nature Genetics, vol. 13, May 1996, pp. 87-90.

Packer et al., "Effect of Oral Milrinone on Mortality in Severe Chronic Heart Failure." The New England Journal of Medicine, vol. 325, No. 21, Nov. 1991, pp. 1468-1475.

Pagel et al., "Influence of levosimendan, pimobendan, and milrinone on the regional distribution of cardiac output in anaesthetized dogs". British Journal of Pharmacology, vol. 119, 1996, pp. 609-615.

(56) References Cited

OTHER PUBLICATIONS

Permanetter et al., "Acute Effects of Intraveneous UD-CG 115 BS (Pimobendan) on the Cardiovascular System and Left Ventricular Pump Function". Journal of Cardiovascular Pharmacology, vol. 14, Supp. 2, 1989, pp. S36-S40.

Piel et al., "Development of a parenteral and of an oral formulation of albendazole with cyclodextrins". S.T.P. Pharma Sciences, vol. 9, No. 3, 1999, pp. 257-260.

Pagel et al., "Comparison of the effects of levosimendn, pimobendan, and milrinone on canine left ventricular-arterial coupling and mechanical efficiency". Basic Respiratory Cardiology, vol. 91, 1996, pp. 296-307.

Stuber et al., "The Pharmaceutical and Biological Availability of Commercial Preparations of Furosemide". Arzneimittel-Forschung, vol. 32, No. 6, 1982, pp. 693-697.

Redenti, E. et al., "Drug/Cyclodextrin/Hydroxy Acid Multicomponent Systems Properties and Pharmaceutical Applications", Journal of Pharmaceutical Sciences, vol. 89, No. 1, Jan. 2000, pp. 1-8.

Lezcano, M. et al., "Complexation of Several Benzimidazole-Type Fungicides with α- and β-Cyclodextrins", Journal of Agricultural and Food Chemistry, vol. 50, No. 1, 2002, pp. 108-112.

Kitzen et al., "Pimobendan". Cardiovascular Drug Reviews, vol. 6, No. 4, 1989, pp. 265-291.

Fraker et al., "Reversal of phosphate induced decreases in force by the benzimidazole pyridazinone, UD-CG 212 CL, in myofilaments from human ventricle." Molecular and Cellular Biochemistry, vol. 176, 1997, pp. 83-88.

Atkins et al., "Pharmacologic management of myxomatous mitral valve disease in dogs." Journal of Veterinary cardiology, vol. 14, 2012, pp. 165-184.

Beaufrere et al., "Therapeutic Review: Pimobendan." Journal of Exotic Pet Medicine, vol. 18, No. 4, Oct. 2009, pp. 311-313.

Boswood et al., "Effect of Pimobendan in Dogs with Preclinical Myxomatous Mitral Valve Disease and cardiomegaly: the EPIC Study—A Randomized Clinical Trial." Journal of Veterinary Internal Medicine, vol. 30, 2016, pp. 1765-1779.

Boswood et al., "Evaluation of pimobendan in dogs with cardiomegaly caused by preclinical mitral valve disease." The Veterinary Record, vol. 168, No. 8, Feb. 2011, p. 222.

Bourezg et al., "Redispersible lipid nanoparticles of Spironolactone obtained by three drying methods." Colloids and Surfaces A: Physicochemical and Engineering Aspects, vol. 413, 2012, pp. 191-199.

El-Badry et al., "Physicochemical Characterization and Dissolution Properties of Meloxicam-Gelucire 50/13 Binary Systems." Scientia Pharmaceutica, vol. 79, 2011, pp. 375-386.

Fasinu et al., "Diverse approaches for the enhancement of oral drug bioavailability." Biopharmaceutics & Drug Disposition, vol. 32, 2011, pp. 185-209.

Fox et al., " Bradykinin-evoked sensitization of airway sensory nerves: A mechanism for ACE-inhibitor cough." Nature Medicine, vol. 2, No. 7, Jul. 1996, pp. 814-817.

Kanno et al., "Effects of Pimobendan for Mitral Valve Regurgitation in Dogs." Journal of Veterinary Medical Science, vol. 69, No. 4, Apr. 2007, pp. 373-377.

Lindenberg et al., "Classification of orally administered drugs on the World Health Organization Model list of Essential Medicines according to the biopharmaceutics classification system." European Journal of Pharmaceutics and Biopharmaceutics, vol. 58, 2004, pp. 265-278.

Nainar et al., "Biopharmaceutical Classification System in In-vitro/In-vivo Correlation: Concept and Development Strategies in Drug Delivery." Tropical Journal of Pharmaceutical Research, vol. 11, No. 2, Apr. 2012, pp. 319-329.

Ouellet et al., "Effect of Pimobendan on Echocardiographic Values in Dogs with Asymptomatic Mitral Valve Disease." Journal of Veterinary Internal Medicine, vol. 23, 2009, pp. 258-263.

Upadhyay et al., "Formulation of Fast-Release Gastroretentive Solid Dispersion of Glibenclamide with Gelucire 50/13." Tropical Journal of Pharmaceutical Research, vol. 11, No. 3, Jun. 2012, pp. 361-369.

Vasconcelos et al., "Solid dispersions as strategy to improve oral bioavailability of poor water soluble drugs." Drug Discovery Today, vol. 12, Nos. 23/24, Dec. 2007, pp. 1068-1075.

Vromans et al., "Densification properties and compactibility of mixtures of pharmaceutical excipients with and without magnesium stearate." International Journal of Pharmaceutics, vol. 46, 1988, pp. 183-192.

Liu et al., "Pharmacology Preparation Technology." Chemical Industry Press, 2006, pp. 113-114.

Sun et al., "Pimobendan." Chemical Industry Press, 2002, pp. 29-30.

\* cited by examiner

PRESERVED ETHERIFIED CYCLODEXTRIN DERIVATIVES CONTAINING LIQUID AQUEOUS PHARMACEUTICAL COMPOSITION

FIELD OF THE INVENTION

The invention relates to the field of medicine, particularly veterinary medicine. In particular, the invention relates to a novel preserved liquid aqueous pharmaceutical composition comprising one or more etherified cyclodextrin derivatives, one or more water-soluble preservatives and at least one pharmaceutically active compound.

BACKGROUND OF THE INVENTION

Cyclodextrins are cyclic oligosaccharides containing six, seven, or eight (α-1,4)-linked D-glucopyranoside units resulting in alpha(α)-, beta(β)- and gamma(γ)-cyclodextrins. In general, cyclodextrins are pharmaceutical excipients that can solubilize various poorly soluble drugs/molecules through the formation of water-soluble drug-cyclodextrin complexes (Loftsson T et al., Journal of Pharmaceutical Sciences 2012, 101(9): 3019-3032). More specifically, cyclodextrins in aqueous solution form inclusion complexes with water-insoluble or poorly soluble drugs by taking up the lipophilic moiety of the drug molecule into the cavity of the cyclodextrin, which is hydrophobic (Brewster M E et al., Advanced Drug Delivery Reviews 2007, 59: 645-666). However, non-inclusion drug-cyclodextrin complexes can also be formed. The higher the cyclodextrin concentration increases, the higher the formation of aggregates of cyclodextrin molecules and self-assembled complexes. A further aspect with cyclodextrin containing pharmaceutical compositions is the formation of self-assembled complexes and/or formation of aggregates (Messner M et al., International Journal of Pharmaceutics 2011, 408: 235-247). Excipients that solubilize and stabilize such aggregates include small ionized molecules such as salts of organic acids and bases.

A substantial problem with pharmaceutical compositions including cyclodextrins is to produce pharmaceutical compositions which are preserved against microbial growth. Such preserved compositions are particularly important for storage of containers containing multiple-dose compositions. Typical preservatives are relatively ineffective at normal concentrations in such compositions, as compositions including such preservatives are unable to meet or pass standard preservative efficacy tests (for example USP <51> or Pharm. Eur. 5.1.3. It is believed that the preservative forms a complex with cyclodextrin and consequently is rendered ineffective or has reduced effectiveness as a preservative. Thus, the preservative loses its full activity by complex formation. The formation of these complexes between preservative and cyclodextrin further reduce the solubility of the active drug substance (Loftsson T et al., Drug Development and Industrial Pharmacy 1992, 18(13): 1477-1484).

Certain etherified β-cyclodextrin derivatives are known to improve solubility of sparingly soluble drugs, see WO 85/02767. However, in WO 85/02767 only the use of etherified β-cyclodextrin derivatives up to a concentration of 10% is described. A molar ratio of drug to etherified β-cyclodextrin derivative of 1:6 to 4:1 was contemplated. The solubility of flubendazol within the above given ratio was only increased by a factor 30. However, those formulations are not suitable for the preparation of pharmaceutical compositions comprising substituted benzimidazole derivatives, such as pimobendan.

Further prior art is as follows:

US 2004/152664 is directed to compositions comprising cyclodextrin derivatives and prednisolone.

WO 2004/089418 deals with a fluoroquinolone comprising aqueous formulations of a pH between 4 and 7.

EP 1 920 785 discloses a liquid preparation comprising a complex of pimobendan and cyclodextrin.

Brewster M E at al. (Advanced Drug Delivery Reviews 2007, 59(7): 645-666) describe cyclodextrins as pharmaceutical solubilizers.

Bassani V L et al. (Journal of Inclusion Phenomena and Molecular Recognition in Chemistry, 1996, 25(1-3): 149-152) refer to the enhanced water-solubility of albendazole by hydroxypropyl-β-cyclodextrin complexation.

The article of Piel G and co-workers (Sciences Techniques et Pratiques STP Pharma Pratiques 1999, 9(3): 257-260) is directed to the development of a parenteral and an oral formulation of albendazole with cyclodextrins.

This enables the development of a pharmaceutical composition for parenteral use but due to the reduced shelf-life of unpreserved compositions, it does not enable the development of a pharmaceutical multiple-dose composition for oral use. Due to the risk of severe tolerance problems and also due to concerns by pet-owners that inflammation in the subcutis following injections is considered to be a risk factor in the development of sarcomas, it is highly desirable to develop an oral pharmaceutical composition.

Due to some animals' intense sense of taste, it is particularly difficult to formulate a medication that can be administered orally and which the animal accepts resulting in an easy to use medication for animals, in particular companion animals, such as dogs, cats and horses (sufficiently good palatability).

The objective underlying the present invention is therefore to provide a pharmaceutical composition which overcomes the problems of the prior art as described above. Particularly, a pharmaceutical composition containing a sparingly water-soluble pharmaceutical active compound at palatable pH values (e.g. ≥pH 3) shall be provided to be administered in adequate form to a subject in need thereof.

SUMMARY OF THE INVENTION

It is therefore provided a preserved liquid aqueous pharmaceutical composition comprising one or more etherified cyclodextrin derivatives; one or more water-soluble preservatives; preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; parabenes and salts thereof, preferably methylparabene, ethylparabene, propylparabene, butylparabene, butylparabene sodium; or combinations thereof; more preferably selected from the group of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; or combinations thereof; and at least one pharmaceutically active compound which is poorly water-soluble, very poorly water-soluble or water-insoluble; wherein preferably the solubility of the at least one pharmaceutically active compound in water in the range of 15 to 25° C. is defined as follows: the at least one pharmaceutically active compound is poorly water-soluble if more than 100 mL of water per gram compound have to be used; it is very poorly water-soluble if more than 1000 mL of water per gram compound have to be used; and it is water-insoluble if more than 10,000 mL water per gram compound have to be used to solubilize the compound; and preferably with the proviso that corticosteroids, in particular prednisolone and its prodrug prednisolone acetate (see US 2004/152664), and fluoroquinolones, in particular ciprofloxacin, gatifloxacin, moxifloxacin, sitafloxacin, lomefloxacin, grepafloxacin, gemifloxacin, norfloxacin, ofloxacin, levofloxacin, trovafloxacin and the like (see WO 2004/089418), are independently from each other excluded as pharmaceutically active compound which is poorly water-soluble, very poorly water-soluble or water-insoluble.

The present invention is also directed to the liquid pharmaceutical composition for use in a method for treating a subject in need of such treatment, preferably an animal, in particular a companion animal, even more preferred horse, dog or cat, guinea pig, hamster, cattle, goat, sheep, in particular cat or dog, selected from among the indications: heart diseases, particularly a hypertrophic cardiomyopathy, more particularly heart failure (HF), congestive heart failure (CHF), acute CHF, decompensated endocardiosis (DCE), dilated cardiomyopathy (DCM), asymptomatic (occult) CHF, asymptomatic DCM, hypertrophic cardiomyopathy (HCM), restricted cardiomyopathy (RCM), and heart failure due to HCM, RCM, DCM and/or UCM.

It is also disclosed a process for producing the pharmaceutical composition comprising the steps, adding at least one pharmaceutically active compound, one or more etherified cyclodextrin derivatives, one or more water-soluble preservatives, optionally one or more antioxidants and optionally at least one water-soluble polymer to water and mixing under stirring, adjusting the pH value using a pH adjustment agent, wherein preferably the one or more water-soluble preservatives are added after the addition of the at least one pharmaceutically active compound.

Subject of the present invention is also a kit of parts that comprises:
  a. a preserved liquid aqueous pharmaceutical composition according to the present invention; and
  b. a package leaflet including the information that the pharmaceutical composition is to be used for the prevention and/or treatment of a heart disease, preferably heart failure and/or hypertrophic cardiomyopathy, in a subject in need of such prevention or treatment.

It is unexpected that the pharmaceutical composition of the present invention can overcome the deficiencies of prior art. The liquid aqueous pharmaceutical compositions for oral administration comprising sparingly or not water-soluble pharmaceutically active compounds, such as pimobendan, known from prior art are usually not suitable due to the low concentration of pharmaceutically active compound normally achieved.

A known pharmaceutically active compound is pimobendan (4,5-dihydro-6-[2-(4-methoxyphenyl)-1H-benzimidazol-5-yl]-5-methyl-3(2H)-pyridazinone) disclosed in EP 0 008 391, herein incorporated by reference in its entirety, and having the formula:

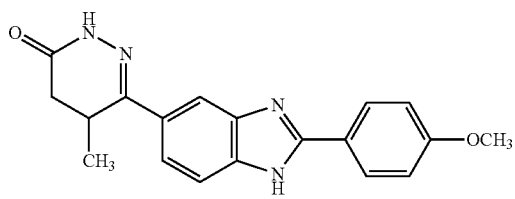 [SMILES: COc1ccc(-c2nc3cc(C4=NNC(=O)CC4C)ccc3[nH]2)cc1]

Pimobendan is a well-known compound for the treatment of congestive heart failure (CHF) originating for example from dilated cardiomyopathy (DCM) or decompensated endocardiosis (DCE) in animals, especially dogs (WO 2005/092343). Furthermore, pimobendan is also used for the treatment of hypertrophic cardiomyopathy in cats (WO 2010/060874). Pimobendan is also approved as a drug product for cardiovascular treatment of humans.

As already described in EP 0 439 030 and WO 2005/08467, pimobendan drug substance is insoluble in water: 1 g drug substance is soluble in more than 10,000 mL. At pH 7 the solubility of pimobendan is only about 0.1 mg per 100 mL.

The solubility of pimobendan in aqueous solutions is depends on the pH. The solubility of pimobendan is significantly higher at pH 1 to 2.5 than at higher pH values (pH 2 3.0). However, the local tolerance and palatability as well as the chemical stability of such a formulation are not acceptable. This is due to the fact that the target dose would require a drug concentration in solution which can only be achieved by a pH of about pH 2.5 and lower. However, the concentration has to be significantly higher, resulting in a low volume that the animal will have to swallow, than is possible at pH≥3.0 in simple aqueous solutions. Accordingly, a pimobendan formulation comprising up to 1.5 mg/mL of pimobendan would need an increase in solubility at pH 7 by a factor of about 1000 to 1500, not achieved in prior art formulations for oral administration up to now.

On the contrary, the preserved liquid aqueous pharmaceutical compositions according to the present invention comprising at least one pharmaceutically active compound which is poorly water-soluble, very poorly water-soluble or water-insoluble with the assistance of one or more etherified cyclodextrin derivatives provides an acceptable solubility of the pharmaceutically active compound such as pimobendan in aqueous solution. Thereby, an acceptable concentration of the pharmaceutically active compound is present allowing for use in an oral administration form.

Further, the one or more water-soluble preservatives present assure an acceptable efficacy of microbial preservation over the required shelf life of the pharmaceutical composition of the present invention.

Furthermore, and unexpectedly, the above water-soluble preservatives retain their effectiveness in the presence of the etherified cyclodextrin derivative(s), i.e. the included water-soluble preservatives do have a substantial preserving efficacy in the presence of cyclodextrin components.

Since the preserved liquid aqueous pharmaceutical compositions according to the present invention may be formulated for oral administration the disadvantageous side effects of parenteral administration such as inflammation in the subcutis following injections may be avoided. In addition, the composition does not have to be given by a veterinarian, as is the case for parenteral administration.

Also the palatability if administered to animal patients is found to be good apparently due to a high concentration of well-palatable etherified cyclodextrin-derivatives present in the pharmaceutical composition of the present invention.

Moreover, the addition of some excipients such as water-soluble polymers and/or antioxidants have been found to be advantageous in order to further increase the concentration of the pharmaceutically active compound to be used and/or to further stabilize the liquid pharmaceutical composition without interfering with the preservative effectiveness of the water-soluble preservatives.

DETAILED DESCRIPTION OF THE INVENTION

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The present invention is based on the surprising unexpected observation that a pharmaceutical composition comprising one or more etherified cyclodextrin derivatives and at least one pharmaceutically active compound can be preserved, without occurrence of the above described deficiencies, in particular that included water-soluble preservatives do have a substantial preserving efficacy in the presence of cyclodextrin components.

According to the present invention a preserved liquid aqueous pharmaceutical composition is provided. The term "aqueous" is to be understood in the meaning that the pharmaceutical composition contains water as a solvent, whereby also one or more additional solvents may be optionally present. According to one preferred embodiments water is the only solvent of such pharmaceutical composition.

The liquid aqueous pharmaceutical composition comprises at least one pharmaceutically active compound which is poorly water-soluble, very poorly water-soluble or water-insoluble. According to the European Pharmacopoeia the solubility of a compound in water in the range of 15 to 25° C. is defined as follows:

| | Solvent in mL per gram compound |
|---|---|
| Very readily soluble | <1 |
| Readily soluble | from 1 to 10 |
| Soluble | from >10 to 30 |
| Hardly soluble | from >30 to 100 |
| Poorly soluble | from >100 to 1,000 |

| | Solvent in mL per gram compound |
|---|---|
| Very poorly soluble | from >1,000 to 10,000 |
| Water-insoluble | >10,000. |

Thus, according to the present invention the at least one pharmaceutically active compound is poorly water-soluble, very poorly water-soluble or water-insoluble. Preferably the at least one pharmaceutically active compound is poorly water-soluble if more than 100 mL of water per gram compound have to be used; it is very poorly water-soluble if more than 1,000 mL of water per gram compound must be used; and it is water-insoluble if more than 10,000 mL water per gram compound have to be used to solubilize the compound.

The at least one pharmaceutically active compound is preferably a benzimidazole derivative. The benzimidazole derivative is preferably a substituted benzimidazole. The term "substituted benzimidazole" as used herein means, but is not limited to thiabendazol, fuberidazol, oxibendazol, parbendazol, cambendazol, mebendazol, fenbendazol, flubendazol, albendazol, oxfendazol, nocodazol, astemisol and pimobendan, pharmaceutically acceptable salts, derivatives, metabolites or prodrugs thereof. Most preferably, the term benzimidazole derivative as used herein means pimobendan, or any pharmaceutically acceptable salts thereof.

In another aspect the at least one pharmaceutically active compound is preferably an oxicam derivative. The oxicam derivative is preferably a substituted oxicam. The term "substituted oxicam" as used herein means, but is not limited to ampiroxicam, droxicam, lornoxicam, piroxicam, tenoxicam and meloxicam, pharmaceutically acceptable salts, derivatives, metabolites or prodrugs thereof. Most preferably, the term oxicam derivative as used herein means meloxicam, or any pharmaceutically acceptable salts thereof.

In another aspect the at least one pharmaceutically active compound is preferably an imidazolinone derivative. The imidazolinone derivative is preferably a substituted imidazolinone. The term "substituted imidazolinone" as used herein means, but is not limited to 1-(4-chlorophenyl)-4-(4-morpholinyl)-2,5-dihydro-1H-imidazol-2-one (imepitoin), pharmaceutically acceptable salts, derivatives, metabolites or prodrugs thereof. Most preferably, the term imidazolinone derivative as used herein means 1-(4-chlorophenyl)-4-(4-morpholinyl)-2,5-dihydro-1H-imidazol-2-one (imepitoin), or any pharmaceutically acceptable salts thereof.

In another aspect the at least one pharmaceutically active compound is preferably a glucopyranosyl-substituted benzene derivative. The glucopyranosyl-substituted benzene derivative is preferably a substituted glucopyranosyl-substituted benzene derivative. The term "substituted glucopyranosyl-substituted benzene derivative" as used herein means, but is not limited to 1-cyano-2-(4-cyclopropyl-benzyl)-4-(β-D-glucopyranos-1-yl)-benzene, pharmaceutically acceptable salts, derivatives, metabolites or prodrugs thereof. Most preferably, the term glucopyranosyl-substituted benzene derivative as used herein means 1-cyano-2-(4-cyclopropyl-benzyl)-4-(β-D-glucopyranos-1-yl)-benzene, or any pharmaceutically acceptable form and/or salt thereof, wherein the pharmaceutically acceptable form preferably is a crystalline complex between 1-cyano-2-(4-cyclopropyl-benzyl)-4-(β-D-glucopyranos-1-yl)-benzene and one or more amino acids, preferably wherein the one or more amino acids is proline, more preferably L-proline.

The liquid aqueous pharmaceutical composition according to the present invention contains the at least one pharmaceutically active compound as disclosed herein, particularly in form of a substituted benzimidazole, more particularly pimobendan, preferably in the range of from 0.01 g/100 mL to 1 g/100 mL, more preferably from 0.05 g/100 mL to 0.5 g/100 mL, most preferably from 0.1 g/100 mL to 0.25 g/100 mL.

Due to the low aqueous solubility of the pharmaceutically active compound as disclosed herein, preferably a substituted benzimidazole, such as pimobendan, at pH values that are acceptable for an oral pharmaceutical composition, one or more solubilizing excipients need to be added to the formulation.

In the present invention such solubilizing excipients are one or more etherified cyclodextrin derivatives.

The liquid aqueous pharmaceutical composition according to the present invention contains the one or more etherified cyclodextrin derivatives preferably in the range of from 5 g/100 mL to 40 g/100 mL more preferably from 10 g/100 mL to 35 g/100 mL, most preferably from 20 g/100 mL to 35 g/100 mL per one etherified cyclodextrin derivative.

The term "etherified cyclodextrin derivative" as used herein includes but is not limited to alpha-, beta- or gamma-cyclodextrin ethers. Preferably the one or more etherified cyclodextrin derivatives as used herein means etherified β-cyclodextrins, more preferably of the chemical formula I:

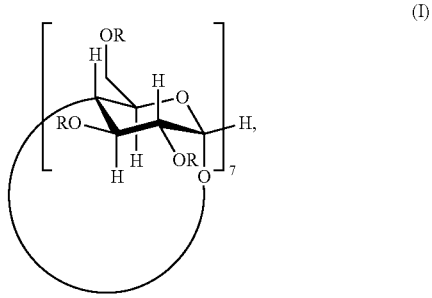

in which the residues R are independently from each other hydroxyalkyl groups and part of the residues R may optionally independently from each other be alkyl groups. A partially etherified β-cyclodextrin of formula I is preferably used, in which the residues R are independently from each other hydroxyethyl, hydroxypropyl or dihydroxypropyl groups. Optionally, part of the residues R may for instance be methyl or ethyl groups.

The use of partially methylated β-cyclodextrins with 7 to 14 methyl groups in the β-cyclodextrin molecule as they are known from DE 31 18 218 does not fall under the present invention.

Partial ethers of β-cyclodextrin comprising only alkyl groups, such as methyl, ethyl and the like, may be particularly suitable in accordance with the invention if they have a low degree of substitution, preferably as defined below of 0.05 to 0.2.

Even more preferably, the one or more etherified cyclodextrin derivatives as used herein are hydroxyethyl-β-cyclodextrin, hydroxypropyl-β-cyclodextrin, dihydroxypropyl-β-cyclodextrin, sulfobutyl-ether-β-cyclodextrin.

Most preferably, the one or more etherified cyclodextrin derivatives as used herein are hydroxypropyl-β-cyclodextrin (HPβCD), referred to as hydroxypropylbetadex in the European Pharmacopoeia. Hydroxypropyl-β-cyclodextrin (HPβCD) of pharmaceutical grade is marketed for example under the trademark CAVASOL® W7 HP Pharma and can be ordered from Wacker, Germany.

Beta-cyclodextrin is a compound with ring structure consisting of 7 anhydro glucose units; it is also referred to as cycloheptaamylose. Each of the 7 glucose rings contains in 2-, 3-, and 6-position three hydroxy groups which may be etherified. In the partially etherified one or more β-cyclodextrin derivatives used according to the invention only part of these hydroxy groups is etherified with hydroxyalkyl groups and optionally further with alkyl groups. When etherifying with hydroxyalkyl groups, which can be carried out by reaction with the corresponding alkylene oxides, the degree of substitution is stated as molar substitution (MS), viz. in mole alkylene oxide per anhydroglucose unit (compare U.S. Pat. No. 3,459,731, column 4). In the hydroxyalkyl ethers of β-cyclodextrin used in accordance with the invention the molar substitution is preferably between 0.05 and 10, more preferably between 0.2 and 2. Particularly preferred is a molar substitution of about 0.40 to about 1.50. The etherification with alkyl groups may be stated directly as degree of substitution (DS) per glucose unit which as stated above is 3 for complete substitution. Partially etherified β-cyclodextrins are used within the invention which preferably comprise besides hydroxyalkyl groups also alkyl groups, especially methyl or ethyl groups, up to a degree of substitution of 0.05 to 2.0, more preferably 0.2 to 1.5. Most preferably the degree of substitution with alkyl groups is between about 0.5 and about 1.2.

As solubilizing excipient hydroxypropyl-β-cyclodextrin (HPβCD) showed very advantageous effects and resulted in the largest increase in solubility of a pharmaceutically active compound to be used such as pimobendan or a pharmaceutically acceptable salt thereof.

To prevent microbial growth in the solution during the in-use period one or more water-soluble preservatives are added to the liquid aqueous pharmaceutical composition. Therefore, the liquid aqueous pharmaceutical composition of the present invention comprises one or more water-soluble preservatives. The one or more water-soluble preservatives are preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; parabenes and salts thereof, preferably methylparabene, ethylparabene, propylparabene, butylparabene, butylparabene sodium; or combinations thereof. In a more preferred embodiment, the one or more water-soluble preservatives are selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; or combinations thereof. Particularly preferred is sorbic acid or salts thereof.

The liquid aqueous pharmaceutical composition according to the present invention contains the one or more water-soluble preservatives preferably in the range of from 0.05 g/100 mL to 3.0 g/100 mL, more preferably from 0.10 g/100 mL to 1.0 g/100 mL, most preferably from 0.20 g/100 mL to 0.40 g/100 mL.

The above disclosed water-soluble preservatives do not displace the pharmaceutically active compound from the cyclodextrin complex. Furthermore, and unexpectedly, the above water-soluble preservatives retain their effectiveness in the presence of the etherified cyclodextrin derivative.

Therefore, the water-soluble preservatives as listed above allow the provision of a preserved cyclodextrin-containing pharmaceutical composition which is particularly suitable for oral and/or parenteral use in veterinary medicine, preferably oral use.

Thus, according to one aspect, the present invention relates to a preserved liquid aqueous pharmaceutical composition comprising one or more etherified cyclodextrin derivatives, one or more water-soluble preservatives and at least one pharmaceutically active compound as disclosed herein, particularly in form of a substituted benzimidazole, more particularly pimobendan, wherein the one or more etherified cyclodextrin derivative is selected from the group consisting of: alpha-, beta-, and/or gamma-cyclodextrin ether.

According to a further aspect, the present invention relates to a preserved liquid aqueous pharmaceutical composition as described above, comprising one or more etherified cyclodextrin derivatives, one or more water-soluble preservatives and at least one pharmaceutically active compound as disclosed herein, particularly in form of a substituted benzimidazole, more particularly pimobendan, wherein the one or more etherified cyclodextrin derivative is etherified β-cyclodextrin. Preferably, that etherified β-cyclodextrin is hydroxyethyl-β-cyclodextrin, hydroxypropyl-β-cyclodextrin, or dihydroxypropyl-β-cyclodextrin. Even more preferably, that etherified β-cyclodextrin is hydroxypropyl-β-cyclodextrin (HPβCD), referred to as hydroxypropylbetadex in the European Pharmacopoeia.

The preserved liquid aqueous pharmaceutical composition according to the present invention may contain one or more excipients. The one or more excipients can be selected from the group consisting of an antioxidant, a water-soluble polymer, buffer, pH adjustment agent, colorants or taste-masking ingredients including flavors.

Preferably at least one water-soluble antioxidant and/or at least one water-soluble polymer may be used. More preferably, at least one water-soluble antioxidant and at least one water-soluble polymer are added as excipients.

In a preferred embodiment, the liquid aqueous pharmaceutical composition of the present invention further comprises at least one water-soluble antioxidant and/or at least one water-soluble polymer, more preferably at least one water-soluble antioxidant and at least one water-soluble polymer.

Thus, according to a preferred embodiment the present invention is directed to a preserved liquid aqueous pharmaceutical composition comprising one or more etherified cyclodextrin derivatives, one or more water-soluble preservatives; preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; parabenes and salts thereof, preferably methylparabene, ethylparabene, propylparabene, butylparabene, butylparabene sodium; or combinations thereof, more preferably selected from the group of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; or combinations thereof; at least one pharmaceutically active compound which is poorly water-soluble, very poorly water-soluble or water-insoluble; preferably with the proviso that corticosteroids, in particular prednisolone and its prodrug prednisolone acetate (see US 2004/152664), and fluoroquinolones, in particular ciprofloxacin, gatifloxacin, moxifloxacin, sitafloxacin, lomefloxacin, grepafloxacin, gemifloxacin, norfloxacin, ofloxacin, levofloxacin, trovafloxacin and the like (see WO 2004/089418), are independently from each other excluded as pharmaceutically active compound which is poorly water-soluble, very poorly water-soluble or water-insoluble; and at least one water-soluble antioxidant.

According to the invention it is preferred that the liquid aqueous pharmaceutical composition comprises at least one water-soluble antioxidant because a combination of a water-soluble preservative and an antioxidant in order to stabilize the water-soluble preservative is particularly preferred. Only a small number of antioxidants are known which are water-soluble and come into question, such as free-radical scavengers, reduction agents and/or chelating agents. Water-soluble antioxidants that can be used comprise ascorbic acid or pharmaceutically acceptable salts thereof, particularly sodium ascorbate; citric acid (anhydrous and/or monohydrate) or pharmaceutically acceptable salts thereof, particularly sodium citrate; erythorbic acid; fumaric acid; malic acid; monothioglycerol; phosphoric acid; sodium metabisulfite; potassium metabisulfite; propionic acid; sodium bisulfite; sodium sulfite; resveratrol, butylhydroxyanisol, gallate derivatives, particularly propylgallate, or combinations thereof, preferably ascorbic acid or pharmaceutically acceptable salts thereof, citric acid (anhydrous and/or monohydrate) or pharmaceutically acceptable salts thereof, sodium metabisulfite, or potassium metabisulfite. Particularly preferred is ascorbic acid or pharmaceutically acceptable salts thereof.

A preservative system comprising one or more water-soluble preservatives preferably in form of an acid or salt thereof and at least one water-soluble antioxidant has been shown to be particularly efficient in preserving the above described liquid aqueous pharmaceutical compositions without having a negative effect on the concentration of the pharmaceutically active compound in the pharmaceutical compositions. Accordingly, in a preferred embodiment, the liquid aqueous pharmaceutically composition of the invention comprises one or more water-soluble preservatives and at least one water-soluble antioxidant.

It was found that in particular sorbic acid or a salt thereof shows advantageous characteristics and preserves the liquid aqueous pharmaceutical composition adequately, albeit at a higher concentration than in solutions not containing a cyclodextrin. From the viewpoint of antimicrobial preservation the pH range of 2.5 to 4.5, in particular 3.5, is advantageous of (1) being in the acidic range (improved antimicrobial activity even without a preservative) and (2) being well below the acid dissociation constant ($pK_a$) value of 4.75 for sorbic acid. Only at pH values below $pK_a$ most of the sorbic acid is present in the protonated (uncharged) state, which is necessary for diffusion through the cell membrane of bacteria and fungi.

Furthermore, the presence of at least one water-soluble antioxidant has a positive influence on the pharmaceutical composition of the present invention:

The water-soluble antioxidant, preferably ascorbic acid or salts thereof, was found to chemically stabilize the one or more water-soluble preservatives, for example sorbic acid or salts thereof, in the formulation. Furthermore, the solubility of the one or more water-soluble preservatives could be increased if at least one antioxidant was present. Tests showed an increase in solubility of sorbic acid by about 0.25% (m/V) by the addition of ascorbic acid.

Furthermore, some water-soluble preservatives such as sorbic acid and potassium sorbate are sensitive to oxidation so that at least one antioxidant should preferably be added.

Small amounts of antioxidant may have a benefit for the pharmaceutical composition according to the present invention.

In a further aspect the liquid aqueous pharmaceutical composition according to the present invention comprises at least one water-soluble antioxidant preferably in the range of from 0.2 g/100 mL to 2.0 g/100 mL, in particular from 0.3 g/100 mL to 1.0 g/100 mL.

In a further aspect the liquid aqueous pharmaceutical composition according to the present invention comprises a ratio of water-soluble preservative and antioxidant preferably being from 0.1 to 10, in particular from 0.1 to 1.5, most preferably from 0.2 to 0.8.

According to the invention it has been found that the concentration of the pharmaceutically active compound that is dissolved with the assistance of one or more etherified cyclodextrin derivatives may be further increased by the addition of at least one water-soluble polymer.

It has been found that the water-soluble polymer does not influence the preservative effectiveness. Furthermore, the described formation of self-assembled complexes and/or formation of aggregates may be further reduced or completely prevented by excipients that solubilize and stabilize such aggregates, e.g. water-soluble polymers such as cellulose derivatives.

In addition, inclusion of such water-soluble polymers in the formulation can be used to optimize the viscosity of the oral solution to ease dosing for example from a plastic syringe.

According to the invention the at least one water-soluble polymer has preferably a molar mass of 5,000 to 500,000 g/mol, more preferably 10,000 to 300,000 g/mol, even more preferred 15,000 to 200,000 g/mol, even more preferred 20,000 to 200,000 g/mol. Examples for said water soluble polymer are hydroxypropyl methylcellulose (hypromellose, HPMC), hydroxypropyl cellulose, carboxymethylcellulose, hydroxyethyl cellulose, hydroxyethylmethyl cellulose, ethylcellulose, methylcellulose, polyvinylpyrrolidone, polyvinylacetate as well as combinations or copolymers thereof, preferably hydroxypropyl methylcellulose (hypromellose).

The liquid aqueous pharmaceutical composition according to the present invention optionally contains the at least one water-soluble polymer preferably in the range of from 0.01 g/100 mL to 0.75 g/100 mL, more preferably from 0.02 g/100 mL to 0.50 g/100 mL, most preferably from 0.05 g/100 mL to 0.30 g/100 mL.

Thus, according to a preferred embodiment the present invention is directed to a preserved liquid aqueous pharmaceutical composition comprising one or more etherified cyclodextrin derivatives; one or more water-soluble preservatives; preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; parabenes and salts thereof, preferably methylparabene, ethylparabene, propylparabene, butylparabene, butylparabene sodium; or combinations thereof, more preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; or combinations thereof; at least one pharmaceutically active compound which is poorly water-soluble, very poorly water-soluble or water-insoluble; preferably with the proviso that corticosteroids, in particular prednisolone and its prodrug prednisolone acetate (see US 2004/152664), and fluoroquinolones, in particular ciprofloxacin, gatifloxacin, moxifloxacin, sitafloxacin, lomefloxacin, grepafloxacin, gemifloxacin, norfloxacin, ofloxacin, levofloxacin, trovafloxacin and the like (see WO 2004/089418), are independently from each other excluded as pharmaceutically active compound which is poorly water-soluble, very poorly water-soluble or water-insoluble; and at least one water-soluble polymer.

According to the invention the pH of the pharmaceutical composition for oral use has preferably a pH value of 2 to 10, more preferably 3 to 10, more preferably 3 to 8, more preferably 3.1 to 8, more preferably 3 to 7, even more preferably 3.2 to 7, even more preferably 2.5 to 5, most preferably 3 to 5. Particularly preferred is pH 3.3 to 6, particularly 3.4 to 5, especially 3.4 to 4. By using the lowest preferred, but still acceptable pH value, it is possible to further increase the solubility of the pharmaceutically active compound as disclosed herein, such as pimobendan, compared to that at higher pH values. Besides the better solubility of the pharmaceutically active compound compared to higher pH values, the lower pH value range has the further advantage of improved preservative efficacy. An improved preservative efficacy results in a lower concentration of a given preservative which is required to achieve an adequate preservative effect.

According to a further preferred embodiment the present invention is directed to a preserved liquid aqueous pharmaceutical composition comprising one or more etherified cyclodextrin derivatives; one or more water-soluble preservatives; preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; parabenes and salts thereof, preferably methylparabene, ethylparabene, propylparabene, butylparabene, butylparabene sodium; or combinations thereof, more preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; or combinations thereof; at least one pharmaceutically active compound which is poorly water-soluble, very poorly water-soluble or water-insoluble; preferably with the proviso that corticosteroids, in particular prednisolone and its prodrug prednisolone acetate (see US 2004/152664), and fluoroquinolones, in particular ciprofloxacin, gatifloxacin, moxifloxacin, sitafloxacin, lomefloxacin, grepafloxacin, gemifloxacin, norfloxacin, ofloxacin, levofloxacin, trovafloxacin and the like (see WO 2004/089418), are independently from each other excluded as pharmaceutically active compound which is poorly water-soluble, very poorly water-soluble or water-insoluble; at least one water-soluble antioxidant; and at least one water-soluble polymer.

According to a further aspect, the present invention relates to a liquid aqueous pharmaceutical composition as described above, comprising at least one pharmaceutically active compound in the form of at least one substituted benzimidazole or a pharmaceutically acceptable salt thereof or a substituted oxicam or a pharmaceutically acceptable salt thereof or a substituted imidazolinone or a pharmaceutically acceptable salt thereof or a substituted glucopyranosyl-substituted benzene derivative or a pharmaceutically acceptable form and/or salt thereof, one or more etherified cyclodextrin derivatives in the form of etherified β-cyclodextrin, one or more water-soluble preservatives, optionally at least one water-soluble polymer and optionally at least one water-soluble antioxidant.

Therefore, the present invention preferably relates to a liquid aqueous pharmaceutical composition as described above, comprising:
  a. at least one pharmaceutically active compound in the form of a substituted benzimidazole or a pharmaceutically acceptable salt thereof, preferably thiabendazol, fuberidazol, oxibendazol, parbendazol, cambendazol, mebendazol, fenbendazol, flubendazol, albendazol, oxfendazol, nocodazol, astemisol or pimobendan, or pharmaceutical acceptable salts thereof, more preferably pimobendan or a pharmaceutically acceptable salt thereof;
  b. one or more etherified cyclodextrin derivatives in the form of etherified β-cyclodextrin, preferably hydroxyethyl-β-cyclodextrin, hydroxypropyl-β-cyclodextrin, dihydroxypropyl-β-cyclodextrin, more preferably hydroxypropyl-β-cyclodextrin (HPβCD);
  c. one or more water-soluble preservatives, preferably selected from the group consisting of sorbic acid or salts thereof, benzoic acid or salts thereof, benzalkonium chloride, benzethonium chloride, cetylpyridinium chloride, sodium metabisulfite, sodium acetate; parabenes and salts thereof, preferably methylparabene, ethylparabene, propylparabene, butylparabene, butylparabene sodium; or combinations thereof, more preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; or combinations thereof, most preferably sorbic acid or salts thereof;
  d. optionally, but according to a preferred embodiment, at least one water-soluble antioxidant, preferably ascorbic acid or a salt thereof; citric acid (anhydrous and/or monohydrate) or a salt thereof; sodium metabisulfite, potassium metabisulfite or resveratrol; and
  e. optionally, but according to a preferred embodiment, at least one water-soluble polymer with a molar mass of 5,000 to 500,000 g/mol, preferably 10,000 to 300,000 g/mol, even more preferred 15,000 to 200,000 g/mol, even more preferred 20,000 to 200,000 g/mol, preferably hydroxypropyl methylcellulose, hydroxypropyl cellulose, or methylcellulose, more preferably hydroxypropyl methylcellulose (hypromellose).

Therefore, the present invention preferably relates to a liquid aqueous pharmaceutical composition as described above, comprising:
  a. at least one pharmaceutically active compound in the form of a substituted oxicam or a pharmaceutically acceptable salt thereof, preferably ampiroxicam, droxicam, lornoxicam, piroxicam, tenoxicam and meloxicam, or pharmaceutical acceptable salts thereof, more preferably meloxicam or a pharmaceutically acceptable salt thereof;
  b. one or more etherified cyclodextrin derivatives in the form of etherified β-cyclodextrin, preferably hydroxyethyl-β-cyclodextrin, hydroxypropyl-β-cyclodextrin, dihydroxypropyl-β-cyclodextrin, more preferably hydroxypropyl-β-cyclodextrin (HPβCD);
  c. one or more water-soluble preservatives, preferably selected from the group consisting of sorbic acid or salts thereof, benzoic acid or salts thereof, benzalkonium chloride, benzethonium chloride, cetylpyridinium chloride, sodium metabisulfite, sodium acetate; parabenes and salts thereof, preferably methylparabene, ethylparabene, propylparabene, butylparabene, butylparabene sodium; or combinations thereof, more preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; or combinations thereof, most preferably sorbic acid or salts thereof;
  d. optionally, but according to a preferred embodiment, at least one water-soluble antioxidant, preferably ascorbic acid or a salt thereof; citric acid (anhydrous and/or monohydrate) or a salt thereof; sodium metabisulfite, potassium metabisulfite or resveratrol; and
  e. optionally, but according to a preferred embodiment, at least one water-soluble polymer with a molar mass of 5,000 to 500,000 g/mol, preferably 10,000 to 300,000 g/mol, even more preferred 15,000 to 200,000 g/mol, even more preferred 20,000 to 200,000 g/mol, preferably hydroxypropyl methylcellulose, hydroxypropyl cellulose, or methylcellulose, more preferably hydroxypropyl methylcellulose (hypromellose).

Therefore, the present invention preferably relates to a liquid aqueous pharmaceutical composition as described above, comprising:
  a. at least one pharmaceutically active compound in the form of a substituted imidazolinone or a pharmaceutically acceptable salt thereof, preferably 1-(4-chlorophenyl)-4-(4-morpholinyl)-2,5-dihydro-1H-imidazol-2-one (imepitoin) or a pharmaceutically acceptable salt thereof;
  b. one or more etherified cyclodextrin derivatives in the form of etherified β-cyclodextrin, preferably hydroxyethyl-β-cyclodextrin, hydroxypropyl-β-cyclodextrin, dihydroxypropyl-β-cyclodextrin, more preferably hydroxypropyl-β-cyclodextrin (HPβCD);
  c. one or more water-soluble preservatives, preferably selected from the group consisting of sorbic acid or salts thereof, benzoic acid or salts thereof, benzalkonium chloride, benzethonium chloride, cetylpyridinium chloride, sodium metabisulfite, sodium acetate; parabenes and salts thereof, preferably methylparabene, ethylparabene, propylparabene, butylparabene, butylparabene sodium; or combinations thereof, more preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; or combinations thereof, most preferably sorbic acid or salts thereof;
  d. optionally, but according to a preferred embodiment, at least one water-soluble antioxidant, preferably ascorbic acid or a salt thereof; citric acid (anhydrous and/or monohydrate) or a salt thereof; sodium metabisulfite, potassium metabisulfite or resveratrol; and e. optionally, but according to a preferred embodiment, at least one water-soluble polymer with a molar mass of 5,000 to 500,000 g/mol, preferably 10,000 to 300,000 g/mol, even more preferred 15,000 to 200,000 g/mol even more preferred 20,000 to 200,000 g/mol, preferably hydroxypropyl methylcellulose, hydroxypropyl cellulose, or methylcellulose, more preferably hydroxypropyl methylcellulose (hypromellose).

Therefore, the present invention preferably relates to a liquid aqueous pharmaceutical composition as described above, comprising:
  a. at least one pharmaceutically active compound in the form of a substituted glucopyranosyl-substituted benzene derivative or a pharmaceutically acceptable salt thereof, preferably 1-cyano-2-(4-cyclopropyl-benzyl)-4-(β-D-glucopyranos-1-yl)-benzene, or pharmaceutical acceptable salts thereof, more preferably 1-cyano-2-(4-cyclopropyl-benzyl)-4-(β-D-glucopyranos-1-yl)-benzene, or any pharmaceutically acceptable form and/or salt thereof, wherein the pharmaceutically acceptable form preferably is a crystalline complex between 1-cyano-2-(4-cyclopropyl-benzyl)-4-(3-D-glucopyranos-1-yl)-benzene and one or more amino acids, preferably wherein the one or more amino acids is proline, more preferably L-proline;
  b. one or more etherified cyclodextrin derivatives in the form of etherified β-cyclodextrin, preferably hydroxyethyl-β-cyclodextrin, hydroxypropyl-β-cyclodextrin, dihydroxypropyl-β-cyclodextrin, more preferably hydroxypropyl-β-cyclodextrin (HPβCD);
  c. one or more water-soluble preservatives, preferably selected from the group consisting of sorbic acid or salts thereof, benzoic acid or salts thereof, benzalkonium chloride, benzethonium chloride, cetylpyridinium chloride, sodium metabisulfite, sodium acetate; parabenes and salts thereof, preferably methylparaben, ethylparaben, propylparaben, butylparaben, butylparaben sodium; or combinations thereof, more preferably selected from the group consisting of sorbic acid or salts thereof, preferably sodium sorbate, potassium sorbate, calcium sorbate; benzoic acid or salts thereof, preferably sodium benzoate; benzalkonium chloride; benzethonium chloride; cetylpyridinium chloride; sodium metabisulfite; sodium acetate; or combinations thereof, most preferably sorbic acid or salts thereof;
  d. optionally, but according to a preferred embodiment, at least one water-soluble antioxidant, preferably ascorbic acid or a salt thereof; citric acid (anhydrous and/or monohydrate) or a salt thereof; sodium metabisulfite, potassium metabisulfite or resveratrol; and
  e. optionally, but according to a preferred embodiment, at least one water-soluble polymer with a molar mass of 5,000 to 500,000 g/mol, preferably 10,000 to 300,000 g/mol, even more preferred 15,000 to 200,000 g/mol, even more preferred 20,000 to 200,000 g/mol, preferably hydroxypropyl methylcellulose, hydroxypropyl cellulose, or methylcellulose, more preferably hydroxypropyl methylcellulose (hypromellose).

The liquid aqueous pharmaceutical composition according to the present invention preferably comprises:
  a. 0.01 g/100 mL to 1 g/100 mL substituted benzimidazole or a pharmaceutically acceptable salt thereof, preferably pimobendan or a pharmaceutically acceptable salt thereof, or a substituted oxicam or a pharmaceutically acceptable salt thereof, preferably meloxicam or a pharmaceutically acceptable salt thereof, or a substituted imidazolinone or a pharmaceutically acceptable salt thereof, preferably 1-(4-chlorophenyl)-4-(4-morpholinyl)-2,5-dihydro-1H-imidazol-2-one (imepitoin) or a pharmaceutically acceptable salt thereof, or a substituted glucopyranosyl-substituted benzene derivative or a pharmaceutically acceptable form and/or salt thereof, preferably 1-cyano-2-(4-cyclopropyl-benzyl)-4-(3-D-glucopyranos-1-yl)-benzene, or any pharmaceutically acceptable form and/or salt thereof, wherein the pharmaceutically acceptable form preferably is a crystalline complex between 1-cyano-2-(4-cyclopropyl-benzyl)-4-(3-D-glucopyranos-1-yl)-benzene and one or more amino acids, preferably wherein the one or more amino acids is proline, more preferably L-proline;
  b. 5 g/100 mL to 40 g/100 mL of one or more etherified cyclodextrin-derivatives, preferably hydroxypropyl-β-cyclodextrin;
  c. 0.05 g/100 mL to 3.0 g/100 mL of at least one water-soluble preservative, preferably sorbic acid or a salt thereof;
  d. optionally, but according to a preferred embodiment, 0.2 g/100 mL to 2.0 g/100 mL of at least one water-soluble antioxidant, preferably ascorbic acid or a salt thereof and
  e. optionally, but according to a preferred embodiment, 0.01 g/100 mL to 0.75 g/100 mL of at least one water-soluble polymer, preferably hydroxypropyl methylcellulose (hypromellose).

According to another aspect the liquid aqueous pharmaceutical composition according to the present invention preferably comprises:
  a. 0.1 g/100 mL to 0.25 g/100 mL pimobendan or a pharmaceutically acceptable salt thereof or meloxicam or a pharmaceutically acceptable salt thereof or 1-(4-chlorophenyl)-4-(4-morpholinyl)-2,5-dihydro-1H-imidazol-2-one (imepitoin) or a pharmaceutically acceptable salt thereof or 1-cyano-2-(4-cyclopropyl-benzyl)-4-(β-D-glucopyranos-1-yl)-benzene, or any pharmaceutically acceptable form and/or salt thereof, wherein the pharmaceutically acceptable form preferably is a crystalline complex between 1-cyano-2-(4-cyclopropyl-benzyl)-4-(β-D-glucopyranos-1-yl)-benzene and one or more amino acids, preferably wherein the one or more amino acids is proline, more preferably L-proline;
  b. 20 g/100 mL to 35 g/100 mL of a hydroxypropyl-β-cyclodextrin;
  c. 0.05 g/100 mL to 0.30 g/100 mL of hydroxypropyl methylcellulose (hypromellose);
  d. 0.20 g/100 mL to 0.40 g/100 mL of a water-soluble preservative, preferably sorbic acid or a salt thereof;
  e. 0.3 g/100 mL to 1.0 g/100 mL of an antioxidant, preferably ascorbic acid or a salt thereof;
  f. wherein optionally the pH of the composition is between 2 to 10, preferably 3 to 10, more preferably 3 to 8, more preferably 3 to 7, more preferably 2.5 to 5, even more preferably 3 to 5, even more preferably 3.4 to 5 and most preferably 3.4 to 4.

With regard to the palatability if administered to animal patients the liquid aqueous pharmaceutically composition is well accepted.

The liquid aqueous pharmaceutical composition provides an acceptable solubility of the pharmaceutically active compound as disclosed herein, such as pimobendan in aqueous solution, according to which a minimum concentration of the pharmaceutically active compound is present allowing for use in an oral administration form. For example, the minimum concentration of pimobendan is preferably 1.5 mg/mL=0.15% (m/V). Furthermore, there is only a negligible crystal growth of the pharmaceutically active compound, if any, during the storage period. Further, the one or more water-soluble preservatives present assure the acceptable efficacy of microbial preservation. In addition, the chemical long-term stability of the active ingredient has been found to be good according to an accelerated stability test in the range of 3.0≤pH≤6.0.

The person skilled in the art knows the effective dosage of pharmaceutically active compounds as disclosed herein, such as benzimidazole derivatives, in particular pimobendan, and is readily able to adjust this dosage which is to be administered to the patient such as an animal patient, in need thereof. In order to have a general guidance in this connection a general therapeutic effective target dose, in particular for the treatment of HCM in cats, is about 0.1 mg to 0.5 mg pimobendan twice daily per kg bodyweight of the animal, preferably about 0.3 mg pimobendan twice daily per kg bodyweight of the animal.

The liquid aqueous pharmaceutical composition according to the present invention is intended for oral and/or parenteral administration, particularly oral solutions may be provided.

According to a preferred embodiment of the present invention the liquid aqueous pharmaceutical composition comprises the pharmaceutically active compound in form of a substituted benzimidazole, preferably pimobendan, or a substituted oxicam, preferably meloxicam, or a substituted imidazolinone, preferably 1-(4-chlorophenyl)-4-(4-morpholinyl)-2,5-dihydro-1H-imidazol-2-one (imepitoin) or a substituted glucopyranosyl-substituted benzene derivative, preferably 1-cyano-2-(4-cyclopropyl-benzyl)-4-(β-D-glucopyranos-1-yl)-benzene, or any pharmaceutically acceptable form and/or salt thereof, wherein the pharmaceutically acceptable form preferably is a crystalline complex between 1-cyano-2-(4-cyclopropyl-benzyl)-4-(β-D-glucopyranos-1-yl)-benzene and one or more amino acids, preferably wherein the one or more amino acids is proline, more preferably L-proline, in a therapeutically effective amount of up to 5 mg/mL, preferably of 1.5 to 4 mg/mL, even more preferably of 1.5 to 3 mg/mL.

According to a further aspect, the present invention also relates to a method of treatment and/or prevention of diseases, wherein cardiotonic, hypotensive, anti-inflammatory and anti-thrombotic substances have a therapeutic benefit, preferably directed to a subject suffering from heart diseases, particularly a hypertrophic cardiomyopathy, comprising the step of administering to such subject in need of such treatment a therapeutically effective amount of any of the liquid aqueous pharmaceutical compositions as described herein.

Preferably, the liquid aqueous pharmaceutical composition of the present invention is administered in a therapeutically effective amount from about 0.075 mg to about 0.5 mg in form of a substituted benzimidazole derivative, preferably pimobendan, or a substituted oxicam, preferably meloxicam, or a substituted imidazolinone preferably 1-(4-chlorophenyl)-4-(4-morpholinyl)-2,5-dihydro-1H-imidazol-2-one (imepitoin) or a substituted glucopyranosyl-substituted benzene derivative, preferably 1-cyano-2-(4-cyclopropyl-benzyl)-4-(β-D-glucopyranos-1-yl)-benzene, or any pharmaceutically acceptable form and/or salt thereof, wherein the pharmaceutically acceptable form preferably is a crystalline complex between 1-cyano-2-(4-cyclopropyl-benzyl)-4-(3-D-glucopyranos-1-yl)-benzene and one or more amino acids, preferably wherein the one or more amino acids is proline, more preferably L-proline, per kg bodyweight of the animal, more preferably from about 0.2 mg to about 0.4 mg of the pharmaceutically active compound in form of a substituted benzimidazole derivative, preferably pimobendan, or a substituted oxicam, preferably meloxicam, or a substituted imidazolinone preferably 1-(4-chlorophenyl)-4-(4-morpholinyl)-2,5-dihydro-1H-imidazol-2-one (imepitoin) or a substituted glucopyranosyl-substituted benzene derivative, preferably 1-cyano-2-(4-cyclopropyl-benzyl)-4-(β-D-glucopyranos-1-yl)-benzene, or any pharmaceutically acceptable form and/or salt thereof, wherein the pharmaceutically acceptable form preferably is a crystalline complex between 1-cyano-2-(4-cyclopropyl-benzyl)-4-(β-D-glucopyranos-1-yl)-benzene and one or more amino acids, preferably wherein the one or more amino acids is proline, more preferably L-proline, per kg bodyweight of the animal, even more preferably about 0.3 mg of the pharmaceutically active compound in form of a substituted benzimidazole derivative, preferably pimobendan, or a substituted oxicam, preferably meloxicam, or a substituted imidazolinone preferably 1-(4-chlorophenyl)-4-(4-morpholinyl)-2,5-dihydro-1H-imidazol-2-one (imepitoin) or a substituted glucopyranosyl-substituted benzene derivative, preferably 1-cyano-2-(4-cyclopropyl-benzyl)-4-(3-D-glucopyranos-1-yl)-benzene, or any pharmaceutically acceptable form and/or salt thereof, wherein the pharmaceutically acceptable form preferably is a crystalline complex between 1-cyano-2-(4-cyclopropyl-benzyl)-4-(β-D-glucopyranos-1-yl)-benzene and one or more amino acids, preferably wherein the one or more amino acids is proline, more preferably L-proline, twice daily per kg bodyweight of the animal. Preferably, two doses are to be administered per day (twice daily administration).

The subject/patient in need of any such treatment mentioned above is a mammal, preferably a companion animal. The term "animal" as used herein includes but is not limited to companion animals such as dogs, cats, guinea pigs, hamsters, horses, cattle, goats, sheep or the like. Preferably, the subject in need of such treatment is a dog, horse or cat, most preferably a cat or dog.

The liquid aqueous pharmaceutical composition according to the present invention is for use in a method for treating a patient in need of such treatment, preferably selected from among the indications: heart failure (HF), congestive heart failure (CHF), acute CHF, decompensated endocardiosis (DCE), dilated cardiomyopathy (DCM), asymptomatic (occult) CHF, asymptomatic DCM, hypertrophic cardiomyopathy (HCM), restricted cardiomyopathy (RCM), and heart failure due to HCM, RCM, DCM and/or UCM.

More preferably, the liquid aqueous pharmaceutical composition according to the present invention is for use in a method for treating a subject in need of such treatment, preferably an animal, in particular a companion animal, even more preferred horse, dog or cat, guinea pig, hamster, cattle, goat, sheep, in particular cat or dog, selected from among the indications: heart diseases, particularly a hypertrophic cardiomyopathy, more particularly heart failure (HF), congestive heart failure (CHF), acute CHF, decompensated endocardiosis (DCE), dilated cardiomyopathy (DCM), asymptomatic (occult) CHF, asymptomatic DCM, hypertrophic cardiomyopathy (HCM), restricted cardiomyopathy (RCM), and heart failure due to HCM, RCM, DCM and/or UCM.

The present invention is also directed to the use of a liquid aqueous pharmaceutical composition as above defined for preparing a pharmaceutical composition for the treatment or prevention of diseases in a subject in need of such treatment, preferably selected from among the above indications.

In a preferred embodiment, the liquid aqueous pharmaceutical composition as defined above for use in the above mentioned methods is for oral and/or parenteral administration, preferably oral administration.

Also subject of the present invention is a kit of parts that comprises:
a. a preserved liquid aqueous pharmaceutical composition as described above; and
b. a package leaflet including the information that the pharmaceutical composition is to be used for the prevention and/or treatment of a heart disease, preferably heart failure and/or hypertrophic cardiomyopathy, in a subject in need of such prevention or treatment.

During the production it has been surprisingly found that it is preferable that the one or more water-soluble preservatives are added after the addition of the at least one pharmaceutically active compound as disclosed herein. In case the one or more water-soluble preservatives are added to the cyclodextrin mixture before the at least one pharmaceutically active compound, the solution may become turbid. If the one or more water-soluble preservatives are added after the at least one pharmaceutically active compound, the produced solution remains clear.

According to a further aspect, the present invention also relates to a manufacturing process for the production of any of the liquid aqueous pharmaceutical compositions as described herein. A process for producing the pharmaceutical composition comprises the steps of: adding at least one pharmaceutically active compound, one or more etherified cyclodextrin derivatives, one or more water-soluble preservatives, optionally one or more antioxidants and optionally at least one water-soluble polymer to water and mixing under stirring, adjusting the pH value using a pH adjustment agent, wherein preferably the one or more water-soluble preservatives are added after the addition of the at least one pharmaceutically active compound.

In this regard it should be taken into account that the process of manufacturing may be arbitrarily selected from manufacturing processes of liquid pharmaceutical compositions known from prior art unless the one or more water-soluble preservatives are added after the addition of the at least one pharmaceutically active compound.

In the following a representative process is described which should not be construed to limit the present invention.

At first, water is weighed in. Optionally, the at least one water-soluble polymer is added, preferably in portions, to the water under stirring until the at least one water-soluble polymer is dissolved thereby obtaining a first liquid mixture. Alternatively, the one or more etherified cyclodextrin derivatives are added to the water under stirring thereby obtaining a first liquid mixture. Alternatively and optionally, the one or more etherified cyclodextrin derivatives are added to the first liquid mixture containing the at least one water-soluble polymer under stirring until the one or more etherified cyclodextrin derivatives are dissolved thereby obtaining a first liquid mixture. Then, an ultrasonic treatment of such first liquid mixture or, preferably under stirring, may be optionally performed. The obtained first liquid mixture or is incubated at room temperature, preferably without stirring, for one or more minutes. Afterwards, the at least one pharmaceutically active compound is added, preferably in portions, under stirring until it is dissolved thereby obtaining a second liquid mixture. Subsequently, the one or more water-soluble preservatives are added, preferably in portions, to the obtained second liquid mixture under stirring until they are dissolved thereby obtaining a third liquid mixture. Optionally, one or more antioxidants as well as further excipients, if so desired, are added, preferably in portions, to the third liquid mixture during stirring thereby obtaining a fourth liquid mixture. Then, an ultrasonic treatment of the fourth liquid mixture, preferably under stirring, is optionally performed. The obtained fourth liquid mixture is incubated at room temperature, preferably without stirring, for one or more minutes. Subsequently, the pH value of the obtained fourth liquid mixture is determined and adjusted, if necessary, using a pH adjustment agent to the desired pH value thereby obtaining the liquid aqueous pharmaceutical composition of the present invention.

The at least one pharmaceutically active compound, one or more etherified cyclodextrin derivatives, one or more water-soluble preservatives, and one or more antioxidants and at least one water-soluble polymer are those as already described in detail supra. The pH adjustment agent is preferably hydrochloric acid and/or sodium hydroxide.

The amounts used depend from the at least one pharmaceutically active compound used as well as the intended treatment, administration route and the patient to be treated. The person skilled in the art is readily able to select and adjust the required amounts by his general knowledge.

The invention described will now be illustrated by figures. However, it is expressly pointed out that the figures are intended solely as an illustration and should not be regarded as restricting the invention.

BRIEF DESCRIPTION OF THE FIGURES

Further advantages, features, characteristics and aspects of the present invention arise from the drawings which show as follows:

FIG. 1 shows a schematic diagram wherein the solubility of pimobendan is indicated as a function of the water-soluble preservatives benzalkonium chloride, benzethonium chloride, cetalpyridinium chloride, sorbic acid, sodium sorbate, benzoic acid, and sodium benzoate, respectively. The last row of columns represents the reference control, which is the respective solution without preservative ("none").

Each water-soluble preservative has been used with pH values of 3.5, 4.5, 5.5, 7, and 9 in combination with a hydroxypropyl-β-cyclodextrin abbreviated as "β" and each water-soluble preservative has been used with pH values of 3.5, 4.5, 5.5, and 7 in combination with a hydroxypropyl-gamma-cyclodextrin abbreviated as "γ". The solutions contain 25% (m/V) cyclodextrin. Each column in the diagram shows the determined solubility of pimobendan as a function of preservative, cyclodextrin type and pH value.

Figure 1:
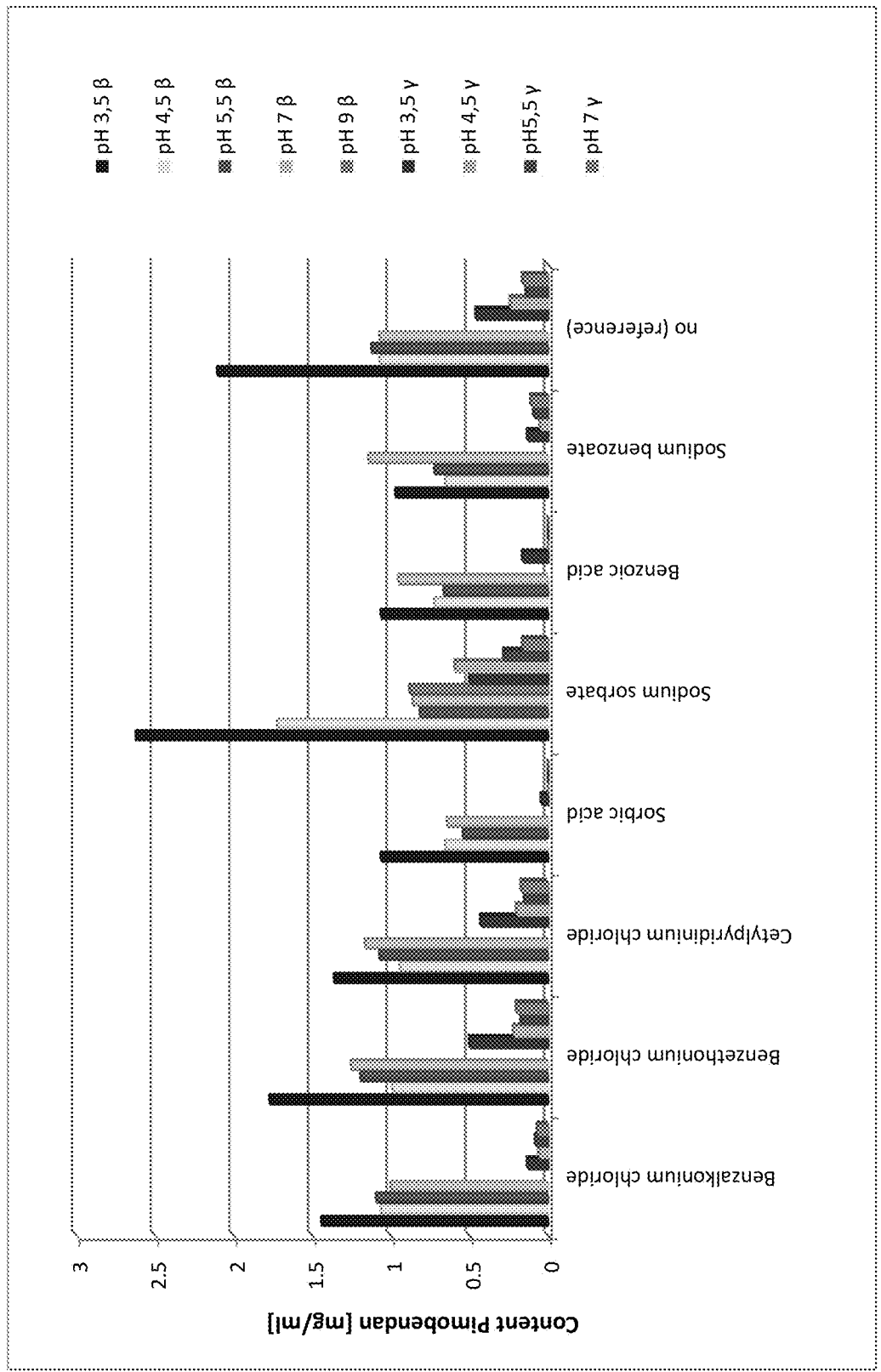
FIG. 1 a schematic diagram wherein the solubility of pimobendan is shown as a function of preservative, cyclodextrin type and pH value in solutions containing 25% (m/V) cyclodextrin.

In FIG. 1 it can be seen that the highest solubility of pimobendan occurs at pH=3.5. Furthermore, pimobendan is more soluble with hydroxypropyl-β-cyclodextrin than hydroxypropyl-gamma-cyclodextrin. The highest pimobendan solubility is achieved with sodium sorbate for which the solubility is significantly higher compared with the results of the reference control wherein no preservative is present.

Figure 2:
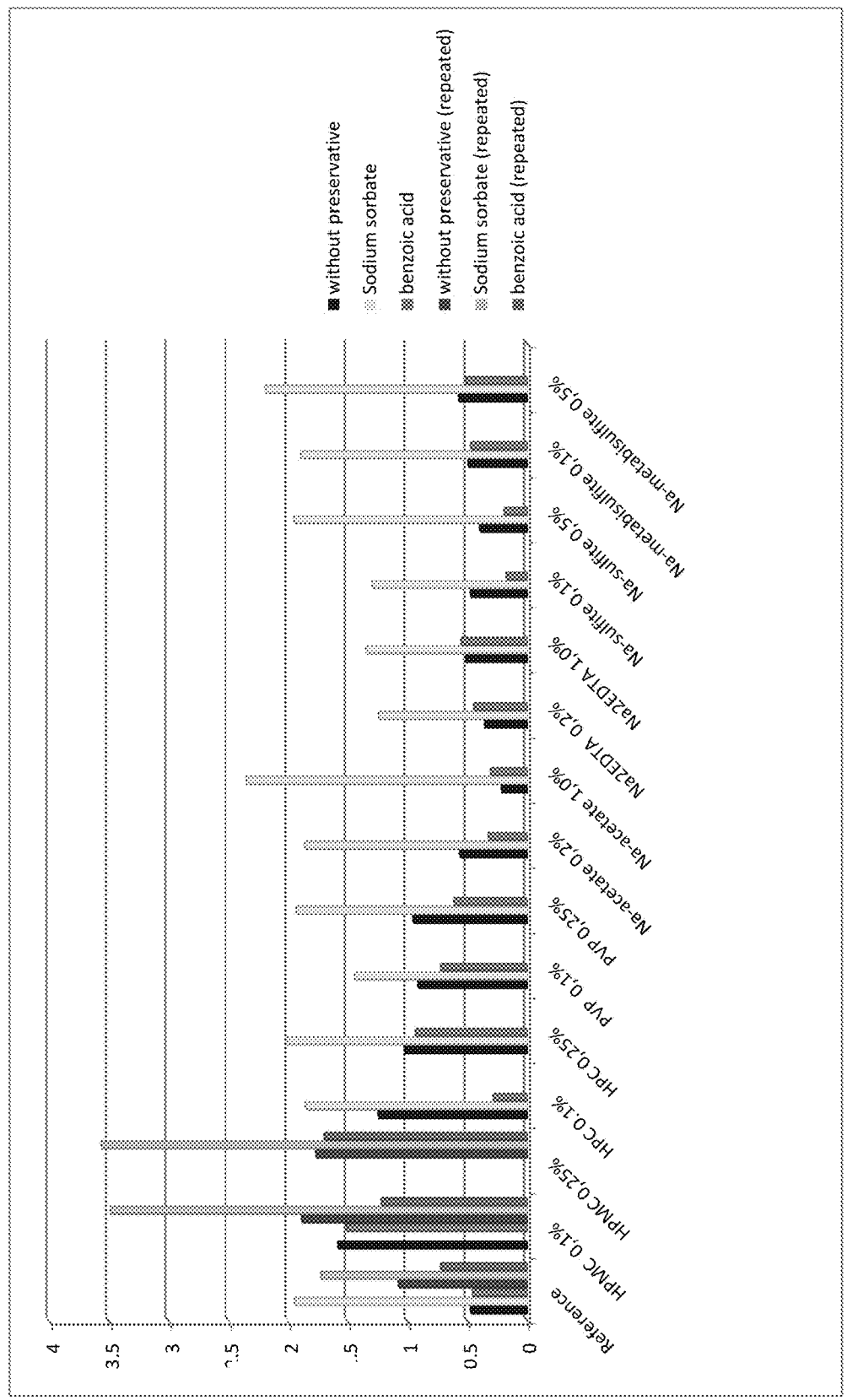
FIG. 2 a schematic diagram wherein the solubility of pimobendan is shown as a function of type and concentration of polymer, salt or complexation agent.

FIG. 2 is a schematic diagram wherein the solubility of pimobendan is shown as a function of type and concentration of polymer, salt or complexation agent. In order to determine the degree of complexation, the effect of three different polymers, three different salts and one chelating agent on the solubility of pimobendan was tested.

The pH of the solution was 4.5. Metolose is hydroxypropyl methylcellulose=HPMC=Hypromellose. Klucel ELF is hydroxypropyl cellulose=HPC. The number after the chemical name indicates the concentration of additive in % (m/V).

The consistency of the reference values [e.g. "sodium sorbate" vs. "sodium sorbate (repeated)"] shows that the results are consistent between the different trials and serves as a plausibility check.

In FIG. 2 it can be seen that the addition of HPMC results in a significant increase in the solubility of pimobendan. The addition of salts or disodium edetate does not significantly increase the solubility of pimobendan.

Figure 3:
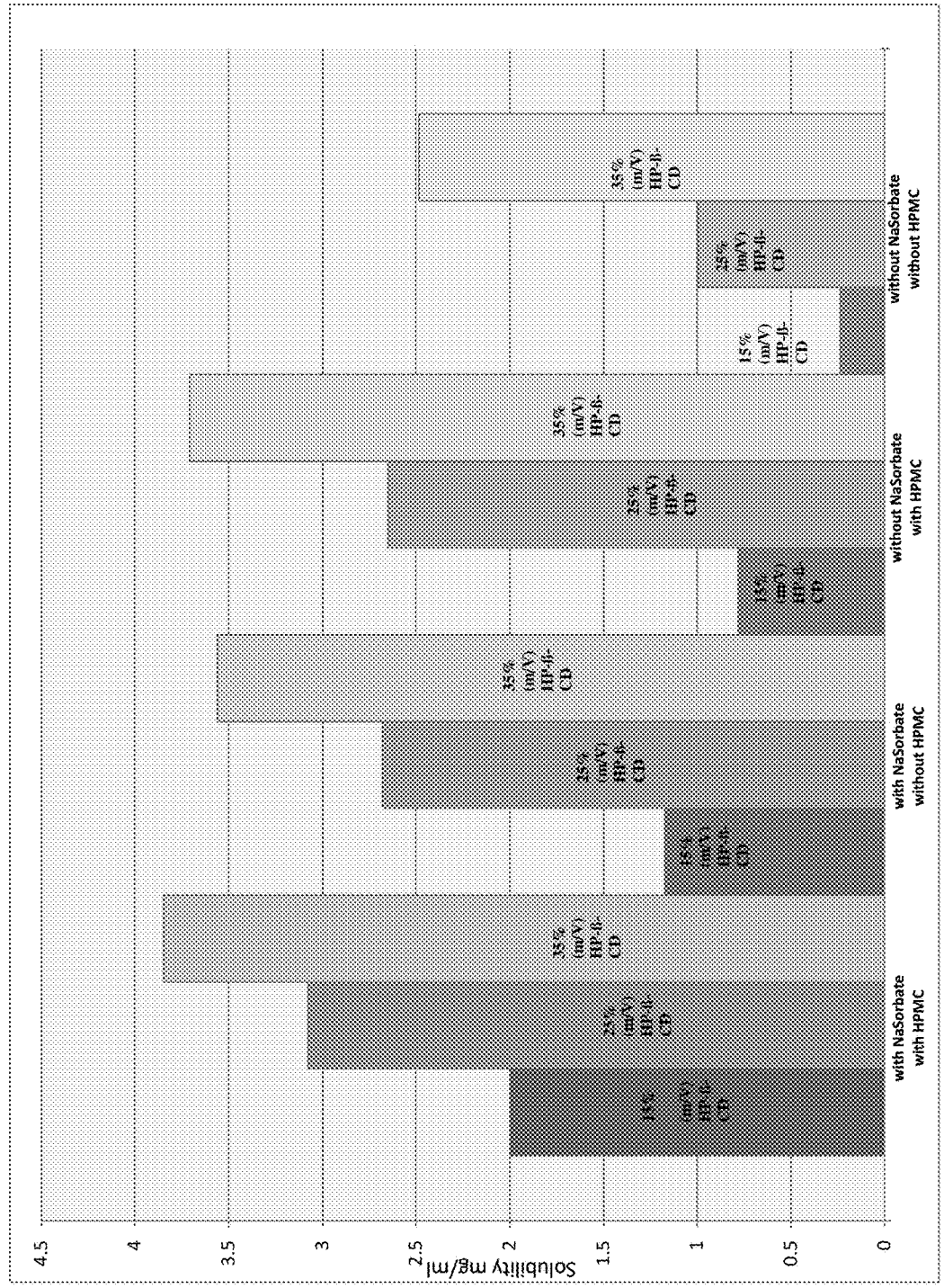
FIG. 3 a schematic diagram wherein the solubility of pimobendan is shown as a function of concentration of hydroxypropyl-β-cyclodextrin and presence of sodium sorbate and hydroxypropyl methylcellulose (HPMC).

FIG. 3 is a schematic diagram wherein the solubility of pimobendan is shown as a function of concentration of hydroxypropyl-β-cyclodextrin and presence of sodium sorbate and hydroxypropyl methylcellulose (HPMC). Therefore, in FIG. 3 the effect of sodium sorbate and HPMC on the solubility of pimobendan was illustrated, and also the effect of concentration of hydroxypropyl-β-cyclodextrin on the pimobendan solubility. Concentrations of sodium sorbate of 1.0% (m/V) and of HPMC of 0.1% (m/V) were used. The pH value was set to 4.5 using hydrochloric acid in all solutions.

In FIG. 3 it can be seen that the results confirm that sodium sorbate significantly increases the solubility of pimobendan. Furthermore, the results also confirm that HPMC significantly increases the solubility of pimobendan. By use of both HPMC and sodium sorbate the solubility of pimobendan is significantly increased.

The invention described will now be illustrated by Examples. However, it is expressly pointed out that the Examples and description are intended solely as an illustration and should not be regarded as restricting the invention. In the following the invention shall be illustrated in form of exemplary pharmaceutical compositions. However, the present invention is not limited to the described compositions, but other components, amounts and additives are possible.

EXAMPLES

Example 1

Manufacturing Process

In the following Table 1 exemplary pharmaceutical compositions according to the present invention are given in detail:

TABLE 1

Exemplary pharmaceutical compositions according to the present invention

| Ingredient | Content [g/100 mL] | Function |
|---|---|---|
| Pimobendan | 0.15-0.25 | Pharmaceutically active compound |
| Hydroxypropyl-β-cyclodextrin | 15-35 | Etherified cyclodextrin |
| Hydroxypropyl methylcellulose | 0.05-2.5 | Water-soluble polymer |
| Sorbic acid and/or potassium sorbate sodium benzoate sodium metabisulfite | 0.1-1.0 | Water-soluble preservative |
| Ascorbic acid and/or sodium ascorbate sodium metabisulfite citric acid sodium citrate | 0.05-1.0 | Antioxidant |
| Hydrochloric acid 0.1M | ad pH 3.1-4.0 | pH adjustment |
| Water | ad 100 mL | Solvent |

The production procedure of an exemplary pharmaceutical composition according to the present invention for a single small scale batch (100 mL) with a target pH value of 3.5 in form of a general instruction is as follows:
1. Weigh purified water. Add a magnetic stirrer.
2. Weigh hydroxypropyl methylcellulose (HPMC) and add in portions to the purified water while stirring.
3. Weigh hydroxypropyl-β-cyclodextrin into a 100 mL glass bottle and add the HPMC solution while stirring until the hydroxypropyl-β-cyclodextrin is dissolved.
4. Let incubate at room temperature without stirring for 10 minutes.
5. Weigh pimobendan and add in portions while stirring until pimobendan is dissolved.
6. Weigh sorbic acid and add in portions while stirring until sorbic acid is dissolved.
7. Weigh ascorbic acid and optionally free-radical scavengers (e.g. BHA or propyl gallate) and add in portions while stirring and nitrogen atmosphere until ascorbic acid and optionally free-radical scavengers are dissolved.
8. Let incubate at room temperature without stirring for 10 minutes.
9. Determine pH and, if necessary, adjust to 3.50.

Example 2

Antimicrobial Efficacy

The testing criteria applied are those for evaluation of antimicrobial activity for oral preparations according to Pharm. Eur. 7(tests at 14 days and 28 days). The acceptance criteria of the Ph. Eur. 7, Method 5.1.3 "Efficacy of Antimicrobial Preservation" USP 34, and Method <51> Antimicrobial Effectiveness Testing are listed in the following Table 2.

TABLE 2

Criteria for evaluation of antimicrobial activity for oral preparations according to Pharm. Eur. 7 and USP 34

| Type of micro-organism | Ph. Eur. 7 Method 5.1.3. Logarithmic reduction of microorganisms after | | USP 34 Method <51> | |
|---|---|---|---|---|
| | 14 days | 28 days | 14 days | 28 days |
| Bacteria | >3 | No increase from 14 days[1] | >1.0 | No increase from 14 days[2] |
| Fungi | >1 | No increase from 14 days[1] | No increase from initial calc. count[2] | No increase from initial calc. count[2] |

[1]for Ph. Eur: No increase = no increase in number
[2]for USP: No increase = not more than 0.5 log$_{10}$ units higher than reference value The formulations tested in the trial are shown in the following Table 3.

The following microorganisms were tested: *Pseudomonas aeruginosa, Straphylococcus aureus, Escherichia coli, Candida albicans, Aspergillus brasiliensis, Zygosaccharomyces rouxi*.

TABLE 3

| Components | Formulation no. | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| | Concentration [g/100 mL] | | | | | | | | | | | | | | | | | | | |
| Pimobendan | | | | | | | | | | 0.15 | | | | | | | | | | |
| HP-β-CD | | | | | | | | | | 25 | | | | | | | | | | |
| HPMC | | | | | | | | | | 0.1 | | | | | | | | | | |
| Sorbic acid | 0.1 | 0.2 | 0.3 | 0.4 | 0.5 | 0.6 | 0.7 | 0.8 | 0.2 | 0.2 | 0.4 | 0.4 | — | — | — | — | — | — | — | — |
| Calcium sorbate | — | — | — | — | — | — | — | — | 0.2 | — | 0.4 | — | — | — | — | — | — | — | — | — |
| Potassium sorbate | — | — | — | — | — | — | — | — | — | 0.2 | — | 0.4 | — | — | — | — | — | — | — | — |
| Sodium benzoate | — | — | — | — | — | — | — | — | — | — | — | — | 0.2 | 0.4 | 0.6 | 0.8 | 1.0 | 0.8 | — | — |
| Benzalk. chloride | — | — | — | — | — | — | — | — | — | — | — | — | — | — | — | — | — | — | 0.1 | 0.1 |
| Ascorbic acid | 0.05 | 0.05 | 0.05 | 0.05 | 0.05 | 0.05 | 0.05 | 0.05 | 0.05 | 0.05 | 0.05 | 0.05 | — | — | — | — | — | 0.05 | — | 0.05 |
| HCl q.s. | | | | | | | | | | ad pH 3.5 | | | | | | | | | | |
| Purified water | | | | | | | | | | ad 100 mL | | | | | | | | | | |

In the performed tests the USP 34 Method <51> Criteria as listed in Table 2 were found to be fulfilled for all solutions for all microorganisms.

Example 3

Formulation Samples were Produced with Compositions Listed in the Following Table 4

TABLE 4

| Ingredient | Formulation No. | | | | | | | | |
|---|---|---|---|---|---|---|---|---|---|
| | 1 | 2 | 3 | 4 | 5 | 6 | 7 | 8 | 9 |
| | Concentration [g/100 mL] | | | | | | | | |
| Pimobendan | — | — | — | — | — | — | — | 0.15 | 0.15 |
| 1-cyano-2-(4-cyclopropyl-benzyl)-4-(β-D-glucopyranos-1-yl)-benzene L-Proline | 0.1 | 0.1 | 0.1 | — | — | — | — | — | — |
| Imepitoin | — | — | — | 0.1 | 0.1 | 0.1 | — | — | — |
| Meloxicam | — | — | — | — | — | — | 0.1 | — | — |
| Hydroxypropyl-β-cyclodextrin | 25 | 25 | 25 | 25 | 25 | 25 | 25 | 25 | 25 |
| Hydroxypropyl methylcellulose | — | 0.1 | 0.1 | — | 0.1 | 0.1 | 0.1 | 0.1 | 0.1 |
| Sorbic acid | 0.3 | — | 0.3 | 0.3 | — | 0.3 | 0.3 | — | — |
| Methyl paraben | — | — | — | — | — | — | — | 0.18 | 0.18 |

TABLE 4-continued

| | Formulation No. | | | | | | | | |
|---|---|---|---|---|---|---|---|---|---|
| | 1 | 2 | 3 | 4 | 5 | 6 | 7 | 8 | 9 |
| Ingredient | Concentration [g/100 mL] | | | | | | | | |
| Propyl paraben | — | — | — | — | — | — | — | 0.02 | 0.02 |
| HCl q.s. ad | pH 3.5 | pH 3.5 | pH 3.5 | pH 3.5 | pH 3.5 | pH 3.5 | pH 3.5 | pH 3.5 | pH 5.0 |
| Water, purified | | | | add 100 mL | | | | | |

The following procedure was used to prepare the samples:
1. Weigh entire amount of water into vessel.
2. Weigh entire amount of hydroxypropyl methylcellulose (HPMC) into a beaker and add slowly to stirred water. Stir until fully dissolved.
3. Weigh entire amount of Hydroxypropyl-β-cyclodextrin (HPβCD) into a beaker and add slowly to stirred mixture. Stir until fully dissolved.
4. Let solution stand at least 10 minutes.
5. Weigh entire amount of drug substance into a beaker and add slowly to stirred mixture. Stir until fully dissolved.
6. Weigh entire amount of sorbic acid into a beaker and add slowly to stirred mixture. Stir until fully dissolved.
7. Let solution stand at least 10 minutes.
8. Adjust pH to target value with HCl or NaOH.
9. Let solutions stand overnight and re-adjust pH to target value with HCl or NaOH.

The solutions were found to have the following densities and appearances:

TABLE 5

| Formulation/Solution | Density [g/mL] | Appearance |
|---|---|---|
| 1 | 1.082 | Clear, colorless, no particles |
| 2 | 1.096 | Clear, colorless, no particles |
| 3 | 1.076 | Clear, colorless, no particles |
| 4 | 1.075 | Clear, colorless, no particles |
| 5 | 1.094 | Clear, colorless, no particles |
| 6 | 1.085 | Clear, colorless, no particles |
| 7 | 1.074 | Clear, light yellow, no particles |
| 8 | 1.080 | Clear, colorless, no particles |
| 9 | 1.082 | Clear, colorless, no particles |

TABLE 6

Microbial results for tested solutions: *E. coli* (bacterium), *P. aeruginosa* (bacterium) and *S. aureus* (bacterium).

| Micro-organism | Solution no. | Colony forming units/g | | | |
|---|---|---|---|---|---|
| | | Innoc. | 7 days | 14 days | 28 days |
| *Escherichia coli* | 1 | 540 000 | <100 | <100 | no data available |
| | 2 | 540 000 | 7300 | 500 | no data available |
| | 3 | 540 000 | <100 | <100 | no data available |
| | 4 | 540 000 | <100 | <100 | no data available |
| | 5 | 540 000 | 48 000 | 2900 | no data available |
| | 6 | 540 000 | <100 | <100 | no data available |
| | 7 | 420 000 | <100 | no data available | no data available |
| | 8 | | | Test not possible[1] | |
| | 9 | | | Test not possible[1] | |
| *Pseudomonas aeruginosa* | 1 | 440 000 | <100 | <100 | no data available |
| | 2 | 440 000 | <100 | <100 | no data available |
| | 3 | 440 000 | <100 | <100 | no data available |
| | 4 | 440 000 | <100 | <100 | no data available |
| | 5 | 440 000 | [2] | 16 000 | no data available |
| | 6 | 440 000 | <100 | <100 | no data available |
| | 7 | 500 000 | <100 | no data available | no data available |
| | 8 | | | Test not possible[1] | |
| | 9 | | | Test not possible[1] | |
| *Staphylococcus aureus* | 1 | 350 000 | <100 | <100 | no data available |
| | 2 | 350 000 | <100 | <100 | no data available |
| | 3 | 350 000 | <100 | <100 | no data available |
| | 4 | 350 000 | <100 | <100 | no data available |
| | 5 | 350 000 | <100 | <100 | no data available |
| | 6 | 350 000 | <100 | <100 | no data available |
| | 7 | 320 000 | <100 | no data available | no data available |
| | 8 | | | Test not possible[1] | |
| | 9 | | | Test not possible[1] | |

[1]Test could not be started due to rapid microbial growth between filtration and start of test
[2]Result not reliable due to high count

TABLE 7

Microbial results for tested solutions: Z. rouxii (yeast fungus), C. albicans (yeast fungus) and A. brasiliensis (mold fungus).

| Micro-organism | Solution no. | Innoc. | 7 days | 14 days | 28 days |
|---|---|---|---|---|---|
| Candida albicans | 1 | 380 000 | <100 | <100 | no data available |
| | 2 | 380 000 | 530 000 | 790 000 | no data available |
| | 3 | 380 000 | <100 | <100 | no data available |
| | 4 | 380 000 | <100 | <100 | no data available |
| | 5 | 380 000 | 500 000 | 660 000 | no data available |
| | 6 | 380 000 | <100 | <100 | no data available |
| | 7 | 370 000 | <100 | no data available | no data available |
| | 8 | | Test not possible[1] | | |
| | 9 | | Test not possible[1] | | |
| Aspergillus brasiliensis | 1 | 120 000 | <100 | 100 | no data available |
| | 2 | 120 000 | 290 000 | 190 000 | no data available |
| | 3 | 120 000 | 7800 | <100 | no data available |
| | 4 | 120 000 | 10 000 | 600 | no data available |
| | 5 | 120 000 | 830 0000 | 740 000 | no data available |
| | 6 | 120 000 | 3000 | 700 | no data available |
| | 7 | 290 000 | 600 | no data available | no data available |
| | 8 | | Test not possible[1] | | |
| | 9 | | Test not possible[1] | | |

[1]Test could not be started due to rapid microbial growth between filtration and start of test It is seen from the results in Table 6 and 7 that a good antimicrobial efficacy is achieved through the use of sorbic acid as a water-soluble preservative. The solutions (no. 2 and 5) with no water-soluble preservative fail the criteria for evaluation of antimicrobial activity according to Ph. Eur. The solutions with methyl paraben and propyl paraben (no. 8 and 9) had such a high microbial growth that the test of antimicrobial efficacy was not possible.

Example 4

Small Amounts of Antioxidant, for Example Ascorbic Acid, Surprisingly Provided an Improvement of the Efficacy of Microbial Preservation

TABLE 8

Formulation compositions in test of efficacy of microbial preservation.

| | Formulation no. | | | |
|---|---|---|---|---|
| | 1 | 2 | 3 | 4 |
| Ingredient | Concentration [g/100 mL] | | | |
| Pimobendan | 0.15 | 0.15 | 0.15 | 0.15 |
| Hydroxypropyl-β-cyclodextrin | 25 | 25 | 25 | 25 |
| Hydroxypropyl methylcellulose | 0.1 | 0.1 | 0.1 | 0.1 |
| Sorbic acid | 0.3 | 0.3 | 0.3 | 0.3 |
| Ascorbic acid | 0.20 | 0.35 | 0.50 | 0.70 |
| HCl q.s. ad | pH 3.5 | pH 3.5 | pH 3.5 | pH 3.5 |
| Water, purified | ad 100 mL | | | |

TABLE 9

Microbiological results according to Pharm. Eur. Method 2.6.12. for the fungi Zygosaccharomyces rouxii, Candida albicans and Aspergillus brasiliensis with varying concentrations of ascorbic acid.

| | Formulation no./incubation period (days) | | | | | | | |
|---|---|---|---|---|---|---|---|---|
| | 1 | | 2 | | 3 | | 4 | |
| Micro-organism | 14 d | 28 d | 14 d | 28 d | 14 d | 28 d | 14 d | 28 d |
| Zygosaccharomyces rouxii | a | a | a | a | a | a | a | a |
| Candida albicans | b | a | a | a | a | a | a | a |
| Aspergillus brasiliensis | c | c | c | b | b | b | b | a |

Codes:
a: <LOQ CFU/mL,
b: LOQ - 1000 CFU/mL,
c: >1000-10 000 CFU/mL,
where CFU = colony forming units and LOQ = limit of quantification The above results demonstrate the increasing efficacy of preservation with increasing concentration of antioxidant, such as ascorbic acid.

Example 5

The formulations according to EP 1 920 785, paragraph [0067] were produced (see table 10).

TABLE 10

| | mg/10 ml | |
|---|---|---|
| Material | Formulation #1 | Formulation #2 |
| Pimobendan | 10.0 | 7.5 |
| Kleptose HP (HP | 3300.0 | 3000.0 |
| Disodium hydrogen phosphate dodecahydrate | 17.6 | 17.6 |
| Sodium dihydogen phosphate dihydrate | 8.0 | 8.0 |
| Methyl paraben | 20.0 | 10.0 |
| Propyl paraben | 5.0 | 5.0 |
| Disodium edetate | 5.0 | 5.0 |
| Water for injection | q.s. to 10 ml | q.s. to 10 ml |

Both formulations were clear, colorless and showed no particles. Formulation #1 has a measured pH of 8.2. Formulation #2 has a measured pH of 7.6.

What is claimed is:

1. A preserved liquid aqueous pharmaceutical composition comprising:
   one or more etherified cyclodextrin derivatives in an amount of 5 g/ml to 40 g/ml;
   one or more water-soluble preservatives in an amount of 0.1 g/ml to 1.0 g/ml, wherein the one or more water-soluble preservatives is sorbic acid or a salt thereof or sorbic acid or a salt thereof in combination with one or more selected from the group consisting of benzoic acid or a salt thereof, benzalkonium chloride, benzethonium chloride, cetylpyridinium chloride, sodium metabisulfite, sodium acetate, and a parabene or a salt thereof;
   at least one water-soluble antioxidant in an amount of 0.05 g/ml to 1.0 g/ml, the at least one water-soluble antioxidant being ascorbic acid or a pharmaceutically acceptable salt thereof or ascorbic acid or a pharmaceutically acceptable salt thereof in combination with one or more selected from the group consisting of citric acid (anhydrous and/or monohydrate) or a pharmaceutically acceptable salt thereof, erythorbic acid, fumaric acid, malic acid, monothioglycerol, phosphoric acid, sodium metabisulfite, potassium metabisulfite, propionic acid, sodium bisulfate, sodium sulfite, resveratrol, butylhydroxyanisol, and a gallate derivative;
   at least one water soluble-polymer in an amount of 0.01 g/ml to 0.75 g/ml; and
   at least one pharmaceutically active compound in an amount of 0.01 g/ml to 1.0 g/ml, the at least one pharmaceutically active compound selected from:
   a benzimidazole derivative; or
   an oxicam derivative; or
   an imidazolinone derivative; or, or
   a glucopyranosyl-substituted benzene derivative.

2. The liquid pharmaceutical composition according to claim 1, wherein the at least one water-soluble antioxidant is selected from the group consisting of sodium ascorbate, sodium citrate, propylgallate, and any one or more combinations thereof.

3. The liquid pharmaceutical composition according to claim 1, wherein the one or more etherified cyclodextrin derivatives comprise etherified β-cyclodextrin having the chemical formula I

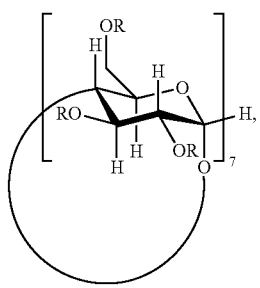

in which the residues R are independently from each other hydroxyalkyl groups.

4. The liquid pharmaceutical composition according to claim 1, wherein the one or more etherified cyclodextrin derivatives comprise hydroxyethyl-β-cyclodextrin, hydroxypropyl-β-cycldextrin, dihydroxypropyl-β-cyclodextrin, or sulphobutyl ether-β-cyclodextrin.

5. The liquid pharmaceutical composition according to claim 1, wherein the at least one water-soluble polymer is selected from hydroxypropyl methylcellulose (hypromellose, HPMC), hydroxypropyl cellulose, carboxymethylcellulose, hydroxyethyl cellulose, hydroxyethylmethyl cellulose, ethylcellulose, methylcellulose, polyvinylpyrrolidone, polyvinylacetate and combinations or copolymers thereof.

6. The liquid pharmaceutical composition according to claim 1, wherein the composition contains the one or more water-soluble preservatives in the range from 0.20 g/100 mL to 0.40 g/100 mL.

7. The liquid pharmaceutical composition according to claim 2, wherein the ratio of water-soluble preservative and antioxidant is from 0.1 to 1.5.

8. The liquid pharmaceutical composition according to claim 1, wherein:
   the at least one pharmaceutically active compound is in the form of:
      a substituted benzimidazole selected from the group consisting of thiabendazol, fuberidazol, oxibendazol, parbendazol, cambendazol, mebendazol, fenbendazol, flubendazol, albendazol, oxfendazol, nocodazol, astemisol, pimobendan, and pharmaceutically acceptable salts thereof; or
      a substituted oxicam selected from the group consisting of ampiroxicam, droxicam, lornoxicam, piroxicam, tenoxicam, meloxicam, and pharmaceutical acceptable salts thereof; or
      a substituted glucopyranosyl-substituted benzene derivative selected from the group consisting of 1-cyano-2-(4-cyclopropyl-benzyl)-4-(β-D-glucopyranos-1-yl)-benzene or any pharmaceutically acceptable form and/or salt thereof, and a crystalline complex between 1-cyano-2-(4-cyclopropyl-benzyl)-4-(β-D-glucopyranos-1-yl)-benzene and one or more amino acids;
   the one or more etherified cyclodextrin derivatives comprise an etherified β-cycldextrin selected from the group consisting of hydroxyethyl-β-cyclodextrin, hydroxypropyl-β-cyclodextrin, and dihydroxypropyl-β-cyclodextrin;
   the composition further comprises sodium metabisulfite, potassium metabisulfite or resveratrol; and
   the at least one water-soluble polymer has a molar mass of 5,000 to 500,000 g/mol.

9. The liquid pharmaceutical composition according to claim 1, wherein the composition comprises:
   0.1 g/100 mL to 0.25 g/100 mL pimobendan or a pharmaceutically acceptable salt thereof; or meloxicam or a pharmaceutically acceptable salt thereof; or 1-(4-chlorophenyl)-4-(4-morpholinyl)-2,5-dihydro-1H-imidazol-2-one (imepitoin) or a pharmaceutically acceptable salt thereof; or 1-cyano-2-(4-cyclopropyl-benzyl)-4-(β-D-glucopyranos-1-yl)-benzene, or any pharmaceutically acceptable form and/or salt thereof;
   20 g/100 mL to 35 g/100 mL of a hydroxypropyl-β-cyclodextrin;
   0.05 g/100 mL to 0.30 g/100 mL of hydroxypropyl methylcellulose (hypromellose);
   0.20 g/100 mL to 0.40 g/100 mL of the water-soluble preservative; and
   0.3 g/100 mL to 1.0 g/100 mL of the antioxidant.

10. The liquid pharmaceutical composition according to claim 1, wherein the pH of the composition is between 2 to 10.

11. The liquid pharmaceutical composition according to claim 1, wherein the composition is for oral and/or parenteral administration.

12. A kit of parts comprising:
a preserved liquid aqueous pharmaceutical composition according claim 1; and
a package leaflet including the information that the pharmaceutical composition is to be used for the prevention and/or treatment of heart failure and/or hypertrophic cardiomyopathy, in a subject in need of such prevention or treatment.

13. The liquid pharmaceutical composition according to claim 1, wherein each water-soluble preservative is selected from the group consisting of sodium sorbate, potassium sorbate, calcium sorbate, sodium benzoate, benzalkonium chloride, benzethonium chloride, cetylpyridinium chloride, sodium metabisulfite, sodium acetate, methylparabene, ethylparabene, propylparabene, butylparabene, butylparabene sodium, and any one or more combinations thereof.

14. The liquid pharmaceutical composition according to claim 1, wherein the ratio of water-soluble preservative to antioxidant is from 0.2 to 0.8.

15. The liquid pharmaceutical composition according to claim 14, wherein the liquid pharmaceutical composition has a pH from 2.5 to 4.5.

16. A preserved liquid aqueous pharmaceutical composition comprising:
one or more etherified cyclodextrin derivatives in an amount of 5 g/ml to 40 g/ml;
one or more water-soluble preservatives in an amount of 0.1 g/ml to 1.0 g/ml, wherein the one or more water-soluble preservatives is sorbic acid or a salt thereof or sorbic acid or a salt thereof in combination with one or more selected from the group consisting of benzoic acid or a salt thereof, benzalkonium chloride, benzethonium chloride, cetylpyridinium chloride, sodium metabisulfite, sodium acetate, and a parabene or a salt thereof;
at least one water-soluble antioxidant in an amount of 0.05 g/ml to 1.0 g/ml, the at least one water-soluble antioxidant being ascorbic acid or a pharmaceutically acceptable salt thereof or ascorbic acid or a pharmaceutically acceptable salt thereof in combination with one or more selected from the group consisting of citric acid (anhydrous and/or monohydrate) or a pharmaceutically acceptable salt thereof, erythorbic acid, fumaric acid, malic acid, monothioglycerol, phosphoric acid, sodium metabisulfite, potassium metabisulfite, propionic acid, sodium bisulfate, sodium sulfite, resveratrol, butylhydroxyanisol, and a gallate derivative;
at least one water soluble-polymer in an amount of 0.01 g/ml to 0.75 g/ml; and
at least one pharmaceutically active compound selected from:
a benzimidazole derivative; or
an oxicam derivative; or
an imidazolinone derivative; or
a glucopyranosyl-sub stituted benzene derivative.

17. The liquid pharmaceutical composition according to claim 1, wherein:
the benzimidazole derivative is selected from the group consisting of thiabendazol, fuberidazol, oxibendazol, parbendazol, cambendazol, mebendazol, fenbendazol, flubendazol, albendazol, oxfendazol, nocodazol, astemisol, pimobendan, and pharmaceutically acceptable salts, derivatives, metabolites or pro-drugs thereof;
the oxicam derivative is selected from the group consisting of ampiroxicam, droxicam, lornoxicam, piroxicam, tenoxicam meloxicam, and pharmaceutically acceptable salts, derivatives, metabolites or pro-drugs thereof;
the imidazolinone derivative comprises 1-(4-chlorophenyl)-4-(4-morpholinyl)-2,5-dihydro-1H-imidazol-2-one (imepitoin), or a pharmaceutically acceptable salt, derivative, metabolite or pro-drug thereof; and
the glucopyranosyl-substituted benzene derivative comprises 1-cyano-2-(4-cyclopropyl-benzyl)-4-(β-D-glucopyranos-1-yl)-benzene, or any pharmaceutically acceptable form and/or salt thereof.

18. The liquid pharmaceutical composition according to claim 1, where the at least one pharmaceutically active compound comprises pimobendan.

19. The liquid pharmaceutical composition according to claim 16, where the at least one pharmaceutically active compound comprises pimobendan.

* * * * *